(12) United States Patent
Narjes et al.

(10) Patent No.: US 8,071,568 B2
(45) Date of Patent: Dec. 6, 2011

(54) NUCLEOSIDE ARYL PHOSPHORAMIDATES FOR THE TREATMENT OF RNA-DEPENDENT RNA VIRAL INFECTION

(75) Inventors: Frank Narjes, Rome (IT); Cristina Gardelli, Rome (IT); Monica Donghi, Rome (IT); Barbara Attenni, Rome (IT); Philippe L. Durette, New Providence, NJ (US)

(73) Assignees: Merck Sharp & Dohme Corp., Rahway, NJ (US); Instituto di Ricerche di Biologia Molecolare P. Angeletti S.p.A., Rome (IT)

( * ) Notice: Subject to any disclaimer, the term of this patent is extended or adjusted under 35 U.S.C. 154(b) by 179 days.

(21) Appl. No.: 12/520,738

(22) PCT Filed: Dec. 28, 2007

(86) PCT No.: PCT/US2007/026468
§ 371 (c)(1),
(2), (4) Date: Jun. 22, 2009

(87) PCT Pub. No.: WO2008/085508
PCT Pub. Date: Jul. 17, 2008

(65) Prior Publication Data
US 2010/0035835 A1    Feb. 11, 2010

Related U.S. Application Data

(60) Provisional application No. 60/878,728, filed on Jan. 5, 2007.

(51) Int. Cl.
*A61K 31/70* (2006.01)
*C07H 19/10* (2006.01)
(52) U.S. Cl. .............................. 514/51; 536/26.8
(58) Field of Classification Search .......... None
See application file for complete search history.

(56) References Cited

U.S. PATENT DOCUMENTS

| | | | |
|---|---|---|---|
| 6,312,662 | B1 | 11/2001 | Erion et al. |
| 6,914,054 | B2 | 7/2005 | Sommadossi et al. |
| 7,429,572 | B2 | 9/2008 | Clark |
| 2005/0009737 | A1 | 1/2005 | Clark |
| 2005/0009775 | A1 | 1/2005 | Howes et al. |
| 2005/0182252 | A1 | 8/2005 | Reddy et al. |
| 2007/0042989 | A1 | 2/2007 | Reddy et al. |
| 2007/0179114 | A1 | 8/2007 | Erion et al. |
| 2007/0265222 | A1 | 11/2007 | MacCoss et al. |

FOREIGN PATENT DOCUMENTS

| | | | |
|---|---|---|---|
| WO | 2006063149 | A1 | 6/2006 |
| WO | 2006121820 | A1 | 11/2006 |
| WO | 2007022073 | A2 | 2/2007 |
| WO | 2007095269 | A2 | 8/2007 |
| WO | 2008079206 | A1 | 7/2008 |

OTHER PUBLICATIONS

Bartenschlager, R. "Candidate Targets for Hepatitis C Virus-Specific Antiviral Therapy", Intervirology, 1997, vol. 40, pp. 378-393.
Crabb, C. "Hard-Won Advances Spark Excitement About Hepatitis C", Science, 2001, vol. 294, pp. 506-507.
Dymock, B. "Emerging therapies for hepatitis C virus infection", Emerging Drugs, 2001, vol. 6, pp. 13-42.
Dymock, B. et al. "Novel approaches to the treatment of hepatitis C virus infection", Antiviral Chemistry & Chemotherapy, 2000, vol. 11, pp. 79-96.
Eldrup, A. et al. "Structure—Activity Relationship of Purine Ribonucleosides for Inhibition of Hepatitis C Virus RNA-Dependent RNA Polymerase", Journal of Medicinal Chemistry, 2004, vol. 47, pp. 2283-2295.
Hoffmann, P. et al. "Recent patents on experimental therapy for hepatitis C virus infection (1999-2002)", Expert Opinion on Therapeutic Patents, 2003, vol. 13, pp. 1707-1723.
Ishi, K. et al. "Expression of Hepatitis C Virus NS5B Protein: Characterization of its RNA Polymerase Activity and RNA Binding", Hepatology, 1999, vol. 29, pp. 1227-1235.
Lauer, G. et al. "Hepatitis C Virus Infection", New England Journal of Medicine, 2001, vol. 345, pp. 41-52.

(Continued)

*Primary Examiner* — Lawrence E Crane
(74) *Attorney, Agent, or Firm* — Kenneth R. Walton; Sheldon O. Heber

(57) ABSTRACT

The present invention provides nucleoside aryl phosphoramidates of structural formula (I) which are precursors to inhibitors of RNA-dependent RNA viral polymerase. These compounds are precursors to inhibitors of RNA-dependent RNA viral replication and are useful for the treatment of RNA-dependent RNA viral infection. They are particularly useful as precursors to inhibitors of hepatitis C virus (HCV) NS5B polymerase, as precursors to inhibitors of HCV replication, and/or for the treatment of hepatitis C infection. The invention also describes pharmaceutical compositions containing such nucleoside aryl phosphoramidates alone or in combination with other agents active against RNA-dependent RNA viral infection, in particular HCV infection. Also disclosed are methods of inhibiting RNA-dependent RNA polymerase, inhibiting RNA-dependent RNA viral replication, and/or treating RNA-dependent RNA viral infection with the nucleoside aryl phosphoramidates of the present invention.

(I)

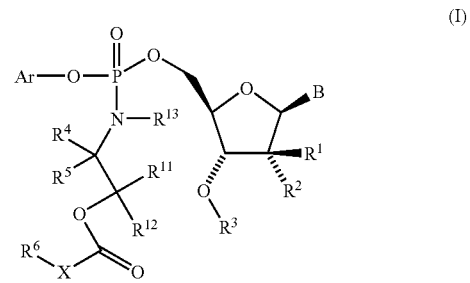

25 Claims, No Drawings

OTHER PUBLICATIONS

Lohmann, V. et al. "Biochemical and Kinetic Analyses of NS5B RNA-Dependent RNA Polymerase of the Hepatitis C Virus", Virology, 1998, vol. 249, pp. 108-118.

McGuigan, C. et al. "Application of Phosphoramidate Pronucleotide Technology to Abacavir Leads to a Significant Enhancement of Antiviral Potency", Journal of Medicinal Chemistry, 2005, vol. 48, pp. 3504-3515.

Moradpour, D. et al. "Current and evolving therapies for hepatitis C", European Journal of Gastroenterology & Hepatology, 1999, vol. 11, pp. 1199-1202.

Rosen H. et al. "Hepatitis C virus: current understanding and prospects for future therapies", Molecular Medicine Today, 1999, vol. 5, pp. 393-399.

Siccardi, D. et al. "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers", The Journal of Pharmacology and Experimental Therapies, 2003. vol. 307, pp. 1112-1119.

Siddiqui, A. et al. "The Presence of Substituents on the Aryl Moiety of the Aryl Phosphoramidate Derivative of d4T Enhances Anti-HIV Efficacy in Cell Culture: A Structure-Activity Relationship", Journal of Medicinal Chemistry, 1999, vol. 42, pp. 393-399.

Uchiyama, M. et al. "O-Selective Phosphorylation of Nucleosides without N-Protection", The Journal of Organic Chemistry, 1993, vol. 58, pp. 373-379.

Walker, M. et al. "Promising candidates for the treatment of chronic hepatitis C", Expert Opinion on Investigational Drugs, 2003, vol. 12, pp. 1269-1280.

NUCLEOSIDE ARYL PHOSPHORAMIDATES FOR THE TREATMENT OF RNA-DEPENDENT RNA VIRAL INFECTION

This application is the National Stage of International Application No. PCT/US2007/026468, filed on Dec. 28, 2007, which claims the benefit of U.S. Provisional Application No. 60/878,728, filed Jan. 5, 2007, the disclosure of which is hereby incorporated by reference in its entirety.

FIELD OF THE INVENTION

The present invention is concerned with nucleoside aryl phosphoramidates, their synthesis, and their use as precursors to inhibitors of RNA-dependent RNA viral polymerase. The compounds of the present invention are precursors to inhibitors of RNA-dependent RNA viral replication and are therefore useful for the treatment of RNA-dependent RNA viral infection. They are particularly useful as precursors to inhibitors of hepatitis C virus (HCV) NS5B polymerase, as precursors to inhibitors of HCV replication, and for the treatment of hepatitis C infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The state of the art in the treatment of HCV infection has been reviewed, and reference is made to the following publications: B. Dymock, et al., "Novel approaches to the treatment of hepatitis C virus infection," *Antiviral Chemistry & Chemotherapy*, 11: 79-96 (2000); H. Rosen, et al., "Hepatitis C virus: current understanding and prospects for future therapies," *Molecular Medicine Today*, 5: 393-399 (1999); D. Moradpour, et al., "Current and evolving therapies for hepatitis C," *European J. Gastroenterol. Hepatol.*, 11: 1189-1202 (1999); R. Bartenschlager, "Candidate Targets for Hepatitis C Virus-Specific Antiviral Therapy," *Intervirology*, 40: 378-393 (1997); G. M. Lauer and B. D. Walker, "Hepatitis C Virus Infection," *N. Engl. J. Med.*, 345: 41-52 (2001); B. W. Dymock, "Emerging therapies for hepatitis C virus infection," *Emerging Drugs*, 6: 13-42 (2001); and C. Crabb, "Hard-Won Advances Spark Excitement about Hepatitis C," *Science*: 506-507 (2001); the contents of all of which are incorporated by reference herein in their entirety.

Different approaches to HCV therapy have been taken, which include the inhibition of viral serine proteinase (NS3 protease), helicase, and RNA-dependent RNA polymerase (NS5B), and the development of a vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. NS5B polymerase is therefore considered to be an essential component in the HCV replication complex [see K. Ishi, et al., "Expression of Hepatitis C Virus NS5B Protein: Characterization of Its RNA Polymerase Activity and RNA Binding," *Hepatology*, 29: 1227-1235 (1999) and V. Lohmann, et al., "Biochemical and Kinetic Analyses of NS5B RNA-Dependent RNA Polymerase of the Hepatitis C Virus," *Virology*, 249: 108-118 (1998)]. Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in M. P. Walker et al., "Promising candidates for the treatment of chronic hepatitis C," *Expert Opin. Invest. Drugs*, 12: 1269-1280 (2003) and in P. Hoffmann et al., "Recent patents on experimental therapy for hepatitis C virus infection (1999-2002)," *Expert Opin. Ther. Patents*," 13: 1707-1723 (2003). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.*, 47: 2283-2295 (2004). There is a continuing need for structurally diverse nucleoside derivatives as inhibitors of HCV polymerase as therapeutic approaches for HCV therapy.

It has now been found that nucleoside aryl phosphoramidates of the present invention are precursors to potent inhibitors of RNA-dependent RNA viral replication and in particular HCV replication. The phosphoramidates are converted in vivo into their nucleoside 5'-phosphate (nucleotide) derivatives which are converted into the corresponding nucleoside 5'-triphosphate derivatives which are inhibitors of RNA-dependent RNA viral polymerase and in particular HCV NS5B polymerase. The instant nucleoside phosphoramidates are useful to treat RNA-dependent RNA viral infection and in particular HCV infection.

It is therefore an object of the present invention to provide nucleoside aryl phosphoramidates which are useful as precursors to inhibitors of RNA-dependent RNA viral polymerase and in particular as precursors to inhibitors of HCV NS5B polymerase.

It is another object of the present invention to provide nucleoside aryl phosphoramidates which are useful as precursors to inhibitors of the replication of an RNA-dependent RNA virus and in particular as precursors to inhibitors of the replication of hepatitis C virus.

It is another object of the present invention to provide nucleoside aryl phosphoramidates which are useful in the treatment of RNA-dependent RNA viral infection and in particular in the treatment of HCV infection.

It is another object of the present invention to provide pharmaceutical compositions comprising the nucleoside aryl phosphoramidates of the present invention in association with a pharmaceutically acceptable carrier.

It is another object of the present invention to provide pharmaceutical compositions comprising the nucleoside aryl phosphoramidates of the present invention for use as precursors to inhibitors of RNA-dependent RNA viral polymerase and in particular as precursors to inhibitors of HCV NS5B polymerase.

It is another object of the present invention to provide pharmaceutical compositions comprising the nucleoside aryl phosphoramidates of the present invention for use as precursors to inhibitors of RNA-dependent RNA viral replication and in particular as precursors to inhibitors of HCV replication.

It is another object of the present invention to provide pharmaceutical compositions comprising the nucleoside aryl phosphoramidates of the present invention for use in the treatment of RNA-dependent RNA viral infection and in particular in the treatment of HCV infection.

It is another object of the present invention to provide pharmaceutical compositions comprising the nucleoside aryl phosphoramidates of the present invention in combination with other agents active against an RNA-dependent RNA virus and in particular against HCV.

It is another object of the present invention to provide methods for the inhibition of RNA-dependent RNA viral polymerase and in particular for the inhibition of HCV NS5B polymerase.

It is another object of the present invention to provide methods for the inhibition of RNA-dependent RNA viral replication and in particular for the inhibition of HCV replication.

It is another object of the present invention to provide methods for the treatment of RNA-dependent RNA viral infection and in particular for the treatment of HCV infection.

It is another object of the present invention to provide methods for the treatment of RNA-dependent RNA viral infection in combination with other agents active against RNA-dependent RNA virus and in particular for the treatment of HCV infection in combination with other agents active against HCV.

It is another object of the present invention to provide nucleoside aryl phosphoramidates and their pharmaceutical compositions for use as a medicament for the inhibition of RNA-dependent RNA viral replication and/or the treatment of RNA-dependent RNA viral infection and in particular for the inhibition of HCV replication and/or the treatment of HCV infection.

It is another object of the present invention to provide for the use of the nucleoside aryl phosphoramidates of the present invention and their pharmaceutical compositions for the manufacture of a medicament for the inhibition of RNA-dependent RNA viral replication and/or the treatment of RNA-dependent RNA viral infection and in particular for the inhibition of HCV replication and/or the treatment of HCV infection.

These and other objects will become readily apparent from the detailed description which follows.

SUMMARY OF THE INVENTION

The present invention relates to compounds of structural formula I of the indicated stereochemical configuration:

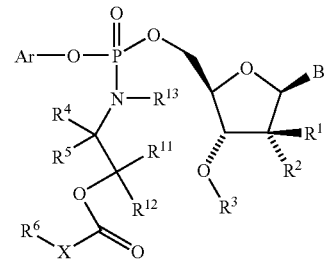

(I)

or a pharmaceutically acceptable salt thereof; wherein

B is

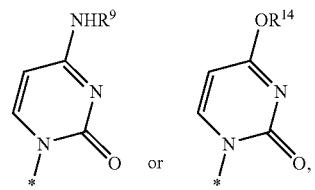

wherein the asterisk (*) denotes the point of attachment to the rest of the compound;

n is 0, 1, or 2;

X is a bond or O;

Ar is phenyl, naphthyl, pyridinyl, pyrimidinyl, pyrazinyl, pyridazinyl, indolyl, quinolinyl, or isoquinolinyl, wherein Ar is optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^1$ is hydrogen, methyl, or fluoromethyl;

$R^2$ is fluoro or $OR^{10}$;

$R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

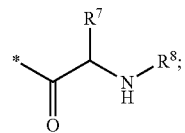

$R^{10}$ is selected from the group consisting of hydrogen, methyl, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

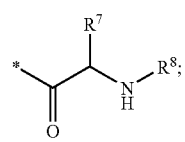

or $R^3$ and $R^{10}$ together with the oxygen atoms to which they are attached form a five-membered cyclic carbonate or an acetonide;

$R^4$ is hydrogen, $C_{1-6}$ alkyl, phenyl, or benzyl;
  wherein alkyl is optionally substituted with one substituent selected from the group consisting of fluorine, hydroxy, methoxy, amino, carboxy, carbamoyl, guanidino, mercapto, methylthio, 1H-imidazolyl, and 1H-indol-3-yl; and wherein phenyl and benzyl are optionally substituted with one to two substituents independently selected from the group consisting of halogen, hydroxy, and methoxy;
$R^5$ is hydrogen or $C_{1-3}$ alkyl;
or $R^4$ and $R^5$ together with the carbon atom to which they are attached form a 3- to 6-membered aliphatic spirocyclic ring system;
$R^6$ is $C_{1-16}$ alkyl, $C_{2-20}$ alkenyl, $(CH_2)_n C_{3-6}$ cycloalkyl, phenyl, benzyl, or adamantyl; wherein alkyl, alkenyl, cycloalkyl, and adamantyl are optionally substituted with one to three substituents independently selected from amino, $C_{1-4}$ alkylamino, di-($C_{1-4}$alkyl)amino, halogen, hydroxy, carboxy, and $C_{1-4}$ alkoxy; and wherein phenyl and benzyl are optionally substituted with one to three substituents independently selected from halogen, hydroxy, cyano, $C_{1-4}$ alkoxy, trifluoromethyl, and trifluoromethoxy;
$R^7$ is hydrogen, $C_{1-5}$ alkyl, or phenyl $C_{0-2}$ alkyl;
$R^8$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl;
$R^9$ is hydrogen, $C_{1-8}$ alkylcarbonyl, or $C_{1-8}$ alkyloxycarbonyl;
$R^{11}$ is hydrogen or $C_{1-3}$ alkyl;
or $R^{11}$ together with $R^{13}$ form a ring of formula:

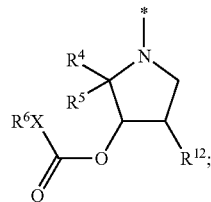

$R^{12}$ is hydrogen or $C_{1-3}$ alkyl;
$R^{13}$ is hydrogen or $C_{1-3}$ alkyl; and
$R^{14}$ is hydrogen, $C_{1-8}$ alkyl, or $C_{1-8}$ alkylcarbonyl.

The compounds of formula I are useful as precursors to inhibitors of RNA-dependent RNA viral polymerase and in particular of HCV NS5B polymerase. They are also precursors to inhibitors of RNA-dependent RNA viral replication and in particular of HCV replication and are useful for the treatment of RNA-dependent RNA viral infection and in particular for the treatment of HCV infection.

Without limitation as to their mechanism of action, the aryl phosphoramidates of the present invention act as precursors of the corresponding nucleoside 5'-monophosphates. Endogenous kinase enzymes convert the 5'-monophosphates into their 5'-triphosphate derivatives which are the inhibitors of the RNA-dependent RNA viral polymerase. Thus, the aryl phosphoramidates may provide for more efficient target cell penetration than the nucleoside itself, may be less susceptible to metabolic degradation, and may have the ability to target a specific tissue, such as the liver, resulting in a wider therapeutic index allowing for lowering the overall dose of the antiviral agent.

Also encompassed within the present invention are pharmaceutical compositions containing the compounds alone or in combination with other agents active against RNA-dependent RNA virus and in particular against HCV as well as methods for the inhibition of RNA-dependent RNA viral replication and for the treatment of RNA-dependent RNA viral infection.

DETAILED DESCRIPTION OF THE INVENTION

The present invention relates to compounds of structural formula I as set forth in the Summary of the Invention above. The compounds of formula I are useful as precursors to inhibitors of RNA-dependent RNA viral polymerase. They are also precursors to inhibitors of RNA-dependent RNA viral replication and are useful for the treatment of RNA-dependent RNA viral infection.

A first embodiment of the present invention is a compound of Formula I-A, or a pharmaceutically acceptable salt thereof:

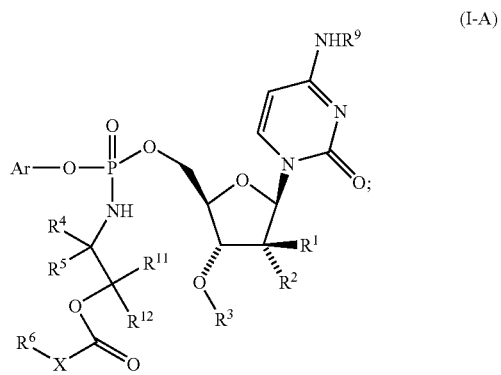

and all variables are as originally defined (i.e., as defined in the Summary of the Invention).

A second embodiment of the present invention is a compound of Formula I-B1, or a pharmaceutically acceptable salt thereof:

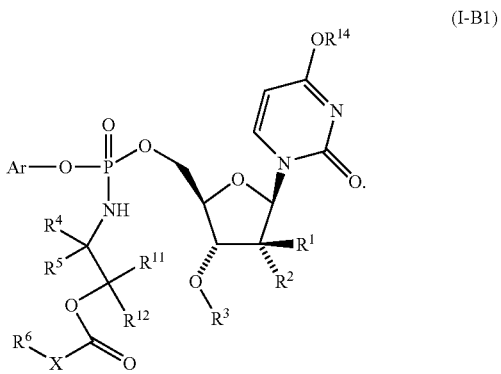

and all variables are as originally defined.

A third embodiment of the present invention is a compound of Formula I-B2, or a pharmaceutically acceptable salt thereof:

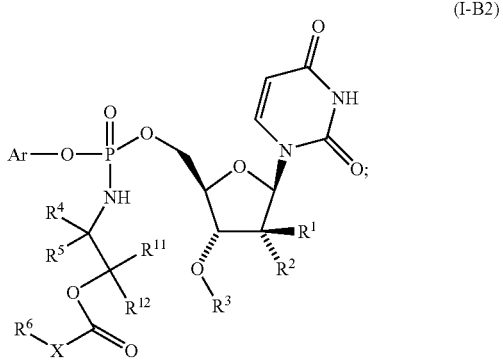

(I-B2)

and all variables are as originally defined.

A fourth embodiment of the present invention is a compound of Formula I-A, or a pharmaceutically acceptable salt thereof, wherein:

$R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

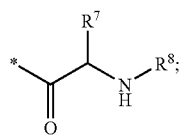

$R^{10}$ is selected from the group consisting of hydrogen, methyl, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

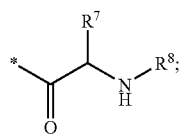

or $R^3$ and $R^{10}$ together with the oxygen atoms to which they are attached form a five-membered cyclic carbonate;

$R^{11}$ is hydrogen or $C_{1-3}$ alkyl; and all other variables are as originally defined.

In a fifth embodiment of the compounds of the present invention, $R^1$ is methyl or fluoromethyl, $R^2$ is hydroxy, and $R^3$ is hydrogen; and all other variables are as originally defined or as defined in the first, second, third, or fourth embodiment. In a class of this embodiment, $R^1$ is methyl.

In a sixth embodiment of the compounds of the present invention, $R^1$ is methyl or fluoromethyl, $R^2$ is fluoro, and $R^3$ is hydrogen; and all other variables are as originally defined or as defined in the first, second, third, or fourth embodiment. In a class of this embodiment, $R^1$ is methyl.

In a seventh embodiment of the compounds of the present invention, X is a bond; and all other variables are as originally defined or as defined in any one of the preceding embodiments.

In an eighth embodiment of the compounds of the present invention, Ar is phenyl optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl; and all other variables are as originally defined or as defined in any one of the preceding embodiments. In a class of this embodiment, Ar is unsubstituted phenyl.

In a ninth embodiment of the compounds of the present invention, Ar is indolyl; and all other variables are as originally defined or as defined in any one of the preceding embodiments. In a class of this embodiment, Ar is 1H-indol-5-yl.

In a tenth embodiment of the compounds of the present invention, $R^5$, $R^{11}$, and $R^{12}$ are each hydrogen and $R^4$ is selected from the group consisting of hydrogen, methyl, ethyl, n-propyl, isopropyl, isobutyl, n-butyl, 2-methyl-1-propyl, hydroxymethyl, fluoromethyl, mercaptomethyl, carboxymethyl, carbamoylmethyl, 1-hydroxyethyl, 2-carboxyethyl, 2-carbamoylethyl, 2-methylthioethyl, 4-amino-1-butyl, 3-amino-1-propyl, 3-guanidino-1-propyl, 1H-imidazol-4-ylmethyl, phenyl, benzyl, 4-hydroxybenzyl, and 1H-indol-3-ylmethyl; and all other variables are as originally defined or as defined in any one of the preceding embodiments. In a class of this embodiment, $R^4$ is methyl or benzyl. In a subclass of this class, $R^4$ is methyl. In another subclass of this class, $R^4$ is benzyl.

In an eleventh embodiment of the compounds of the present invention, X is a bond, and $R^6$ is $C_{1-8}$ alkyl, cyclohexyl, or cyclopentyl; and all other variables are as originally defined or as defined in any one of the preceding embodiments. In a class of this embodiment, $R^6$ is $C_{1-4}$ alkyl.

In a twelfth embodiment of the compounds of the present invention, X is a bond, Ar is phenyl, $R^4$ is methyl or benzyl, $R^6$ is $C_{1-4}$ alkyl, and $R^5$, $R^{11}$, and $R^{12}$ are each hydrogen; and all other variables are as originally defined or as defined in any one of the preceding embodiments. In a class of this embodiment, $R^1$ is methyl, $R^2$ is hydroxy, and $R^3$ is hydrogen.

A thirteenth embodiment of the present invention is a compound of Formula II-A, or a pharmaceutically acceptable salt thereof:

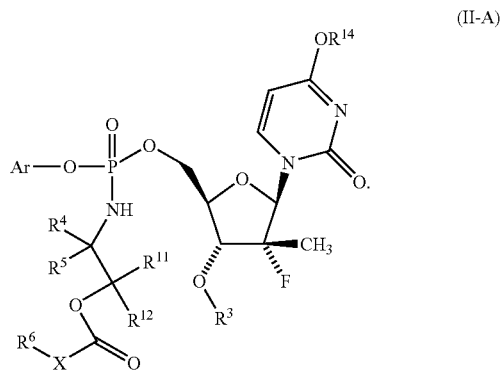

(II-A)

wherein the variables are as originally defined or as defined in any one of the preceding embodiments.

A fourteenth embodiment of the present invention is a compound of Formula II-B, or a pharmaceutically acceptable salt thereof:

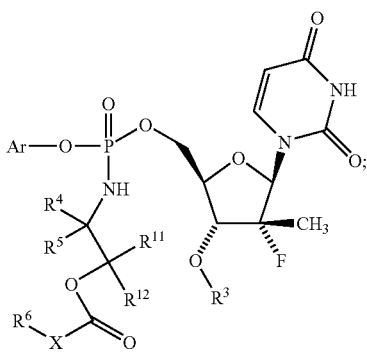

(II-B)

wherein the variables are as originally defined or as defined in any one of the preceding embodiments.

A fifteenth embodiment of the present invention is a compound of Formula III, or a pharmaceutically acceptable salt thereof:

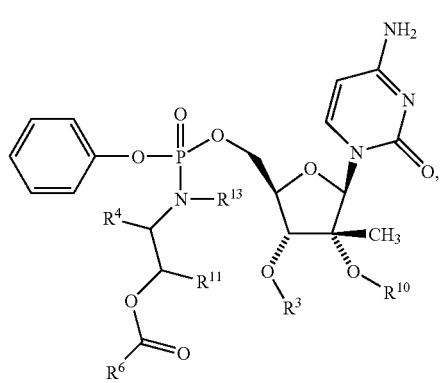

(III)

wherein:
$R^3$ is H;
$R^{10}$ is H;
or $R^3$ and $R^{10}$ together with the oxygen atoms to which they are attached form acetonide;
$R^4$ is H, methyl, ethyl, propyl, isopropyl, n-butyl, isobutyl, t-butyl, $CH(CH_3)CH_2CH_3$, or benzyl;
$R^6$ is methyl, ethyl, n-propyl, isopropyl, n-butyl, isobutyl, t-butyl, $CH(CH_2CH_2CH_3)_2$, 3-pentyl, cyclopentyl, cycloheptyl, or phenyl;
$R^{11}$ is H or $CH_3$;
$R^{13}$ is hydrogen or $CH_3$;
or, alternatively when $R^4$ is H, $R^{11}$ together with $R^{13}$ form a ring of formula:

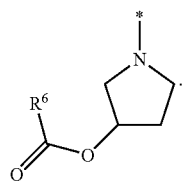

A sixteenth embodiment of the present invention is a compound of Formula I which is selected from the group consisting of the compounds set forth in Examples 1 to 22 and pharmaceutically acceptable salts thereof. In a sub-embodiment, the compounds are selected from the group consisting of the compounds set forth in Examples 1 to 8 and pharmaceutically acceptable salts thereof.

In one embodiment of the present invention, the nucleoside aryl phosphoramidates of the present invention are useful as precursors to inhibitors of positive-sense single-stranded RNA-dependent RNA viral polymerase, inhibitors of positive-sense single-stranded RNA-dependent RNA viral replication, and/or for the treatment of positive-sense single-stranded RNA-dependent RNA viral infection. In a class of this embodiment, the positive-sense single-stranded RNA-dependent RNA virus is a Flaviviridae virus or a Picornaviridae virus. In a subclass of this class, the Picornaviridae virus is a rhinovirus, a poliovirus, or a hepatitis A virus. In a second subclass of this class, the Flaviviridae virus is selected from the group consisting of hepatitis C virus, yellow fever virus, dengue virus, West Nile virus, Japanese encephalitis virus, Banzi virus, and bovine viral diarrhea virus (BVDV). In a subclass of this subclass, the Flaviviridae virus is hepatitis C virus.

Another aspect of the present invention is concerned with a method for inhibiting RNA-dependent RNA viral polymerase, a method for inhibiting RNA-dependent RNA viral replication, and/or a method for treating RNA-dependent RNA viral infection in a mammal in need thereof comprising administering to the mammal a therapeutically effective amount of a compound of structural formula I.

In one embodiment of this aspect of the present invention, the RNA-dependent RNA viral polymerase is a positive-sense single-stranded RNA-dependent RNA viral polymerase. In a class of this embodiment, the positive-sense single-stranded RNA-dependent RNA viral polymerase is a Flaviviridae viral polymerase or a Picornaviridae viral polymerase. In a subclass of this class, the Picornaviridae viral polymerase is rhinovirus polymerase, poliovirus polymerase, or hepatitis A virus polymerase. In a second subclass of this class, the Flaviviridae viral polymerase is selected from the group consisting of hepatitis C virus polymerase, yellow fever virus polymerase, dengue virus polymerase, West Nile virus polymerase, Japanese encephalitis virus polymerase, Banzi virus polymerase, and bovine viral diarrhea virus (BVDV) polymerase. In a subclass of this subclass, the Flaviviridae viral polymerase is hepatitis C virus polymerase.

In a second embodiment of this aspect of the present invention, the RNA-dependent RNA viral replication is a positive-sense single-stranded RNA-dependent RNA viral replication. In a class of this embodiment, the positive-sense single-stranded RNA-dependent RNA viral replication is Flaviviridae viral replication or Picornaviridae viral replication. In a subclass of this class, the Picornaviridae viral replication is rhinovirus replication, poliovirus replication, or hepatitis A virus replication. In a second subclass of this class, the Flaviviridae viral replication is selected from the group consisting of hepatitis C virus replication, yellow fever virus replication, dengue virus replication, West Nile virus replication, Japanese encephalitis virus replication, Banzi virus replication, and bovine viral diarrhea virus replication. In a subclass of this subclass, the Flaviviridae viral replication is hepatitis C virus replication.

In a third embodiment of this aspect of the present invention, the RNA-dependent RNA viral infection is a positive-sense single-stranded RNA-dependent viral infection. In a class of this embodiment, the positive-sense single-stranded RNA-dependent RNA viral infection is Flaviviridae viral infection or Picornaviridae viral infection. In a subclass of this class, the Picornaviridae viral infection is rhinovirus infection, poliovirus infection, or hepatitis A virus infection. In a second subclass of this class, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. In a subclass of this subclass, the Flaviviridae viral infection is hepatitis C virus infection.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "naphthyl" encompasses both 1-naphthyl (α-naphthyl) and 2-naphthyl (β-naphthyl).

The term "adamantyl" encompasses both 1-adamantyl and 2-adamantyl.

By the term "optionally substituted benzyl" is meant —CH$_2$-phenyl wherein the phenyl moiety is optionally substituted.

The term "alkenyl" shall mean straight or branched chain alkenes of two to twenty total carbon atoms, or any number within this range (e.g., ethenyl, propenyl, butenyl, pentenyl, oleyl, etc.).

The term "cycloalkyl" shall mean cyclic rings of alkanes of three to eight total carbon atoms, or any number within this range (e.g., cyclopropyl, cyclobutyl, cyclopentyl, cyclohexyl, cycloheptyl, or cyclooctyl).

The term "alkoxy" refers to straight or branched chain alkoxides of the number of carbon atoms specified (e.g., $C_{1-4}$ alkoxy), or any number within this range [e.g., methoxy (MeO—), ethoxy, isopropoxy, etc.].

The term "alkylthio" refers to straight or branched chain alkylsulfides of the number of carbon atoms specified (e.g., $C_{1-4}$ alkylthio), or any number within this range [e.g., methylthio (MeS—), ethylthio, isopropylthio, etc.].

The term "alkylamino" refers to straight or branched alkylamines of the number of carbon atoms specified (e.g., $C_{1-4}$ alkylamino), or any number within this range [e.g., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [e.g., methylsulfonyl (MeSO$_2$—), ethylsulfonyl, isopropylsulfonyl, etc.].

The term "alkyloxycarbonyl" refers to straight or branched chain esters of a carboxylic acid or carbamic acid group present in a compound of the present invention having the number of carbon atoms specified (e.g., $C_{1-8}$ alkyloxycarbonyl), or any number within this range [e.g., methyloxycarbonyl (MeOCO—), ethyloxycarbonyl, or butyloxycarbonyl].

The term "alkylcarbonyl" refers to straight or branched chain alkyl acyl group of the specified number of carbon atoms (e.g., $C_{1-8}$ alkylcarbonyl), or any number within this range [e.g., methyloxycarbonyl (MeOCO—), ethyloxycarbonyl, or butyloxycarbonyl].

The term "halogen" is intended to include the halogen atoms fluorine, chlorine, bromine and iodine.

An asterisk (*) at the end of a bond denotes the point of attachment to the rest of the compound.

The term "phosphoryl" refers to —P(O)(OH)$_2$.

The term "diphosphoryl" refers to the radical having the structure:

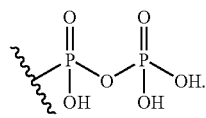

The term "triphosphoryl" refers to the radical having the structure:

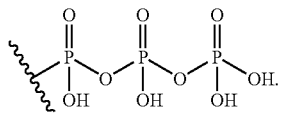

The term "five-membered cyclic carbonate ring" denotes the following ring system formed at the C-2 and C-3 positions of the furanose ring of the nucleoside by acylating the C-2 and C-3 hydroxyls with a carbonylating reagent, such as phosgene and 1,1'-carbonyldiimidazole:

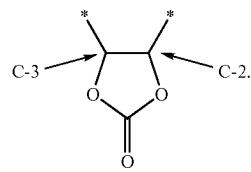

The term "acetonide" denotes the following ring system formed at the C-2 and C-3 positions of the furanose ring of the nucleoside:

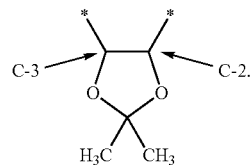

When $R^7$ in the amino acyl residue embodiment of $R^3$ and $R^{10}$ is a substituent other than hydrogen in the formula

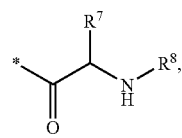

the amino acyl residue contains an asymmetric center and is intended to include the individual R- and S-stereoisomers as well as RS-diastereoisomeric mixtures. In one embodiment, the stereochemistry at the stereogenic carbon corresponds to that of an S-amino acid, that is, the naturally occurring alpha-amino acid stereochemistry, as depicted in the formula:

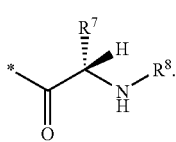

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally.

The term "5'-triphosphate" refers to a triphosphoric acid ester derivative of the 5'-hydroxyl group of a nucleoside compound of the present invention having the following general structural formula IV:

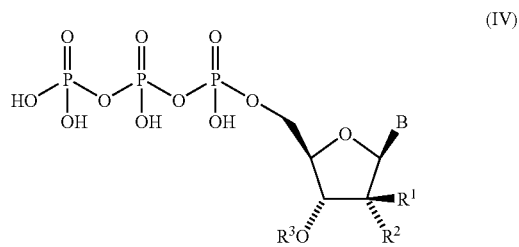

wherein B, $R^1$, $R^2$, and $R^3$ are as defined above. In aspects of this definition, the term refers to either or both of the derivatives of formula IV-A and IV-B:

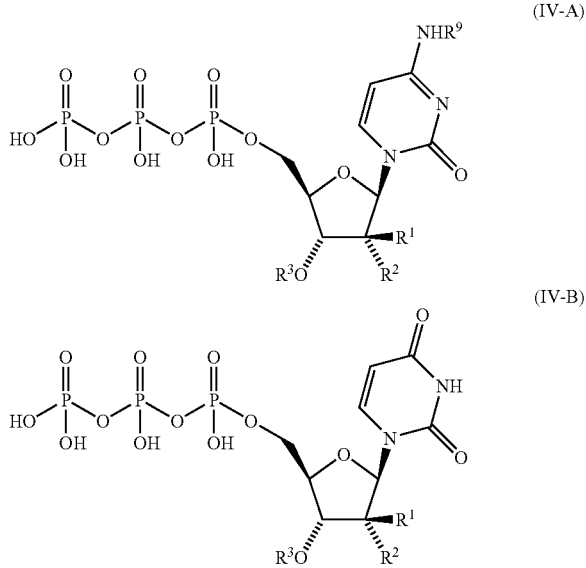

The term "composition", as in "pharmaceutical composition," is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Another aspect of the present invention is concerned with a method of inhibiting HCV NS5B polymerase, inhibiting HCV replication, or treating HCV infection with a compound of the present invention in combination with one or more agents useful for treating HCV infection. Such agents active against HCV include, but are not limited to, ribavirin, levovirin, viramidine, nitazoxanide, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection. When a compound of the present invention or a pharmaceutically acceptable salt thereof is used in combination with a second therapeutic agent active against HCV, the dose of each compound may be either the same as or different from the dose when the compound is used alone.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/18369, WO 02/08244, WO 02/48116, WO 02/48172, WO 05/037214, and U.S. Pat. No. 6,323,180. HCV NS3 protease as a target for the development of inhibitors of HCV replication and for the treatment of HCV infection is discussed in B. W. Dymock, "Emerging therapies for hepatitis C virus infection," *Emerging Drugs*, 6: 13-42 (2001). Specific HCV NS3 protease inhibitors combinable with the compounds of the present invention include BILN2061, VX-950, $SCH_6$, $SCH_7$, and SCH-503034.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.*, 62: 1754-1759 (1997); M. S. Wolfe, et al., *Tetrahedron Lett.*, 36: 7611-7614 (1995); U.S. Pat. No. 3,480, 613 (Nov. 25, 1969); U.S. Pat. No. 6,777,395 (Aug. 17, 2004); U.S. Pat. No. 6,914,054 (Jul. 5, 2005); International Publication Numbers WO 01/90121 (29 Nov. 2001); WO 01/92282 (6 Dec. 2001); WO 02/32920 (25 Apr. 2002); WO 02/057287 (25 Jul. 2002); WO 02/057425 (25 Jul. 2002); WO 04/002422 (8 Jan. 2004); WO 04/002999 (8 Jan. 2004); WO 04/003000 (8 Jan. 2004); WO 04/002422 (8 Jan. 2004); US Patent Application Publications 2005/0107312; US 2005/0090463; US 2004/0147464; and US 2004/0063658; the contents of each of which are incorporated by reference in their entirety. Such 2'-C-branched ribonucleosides include, but are not limited to, 2'-C-methylcytidine, 2'-fluoro-2'-C-methylcytidine 2'-C-methyluridine, 2'-C-methyladenosine, 2'-C-methylguanosine, and 9-(2-C-methyl-β-D-ribofuranosyl)-2,6-diaminopurine; the corresponding amino acid esters of the furanose C-2', C-3', and C-5' hydroxyls (such as 3'-O-(L-valyl)-2'-C-methylcytidine dihydrochloride, also referred to as valopicitabine dihydrochloride or NM-283 and 3'-O-(L-valyl)-2'-fluoro-2'-C-methylcytidine), and the corresponding optionally substituted cyclic 1,3-propanediol esters of their 5'-phosphate derivatives.

The compounds of the present invention may also be combined for the treatment of HCV infection with other nucleosides having anti-HCV properties, such as those disclosed in U.S. Pat. No. 6,864,244 (Mar. 8, 2005); WO 02/51425 (4 Jul. 2002), assigned to Mitsubishi Pharma Corp.; WO 01/79246, WO 02/32920, and WO 02/48165 (20 Jun. 2002), assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), assigned to Hoffmann-LaRoche; U.S. 2002/0019363 (14 Feb. 2002); WO 02/100415 (19 Dec. 2002); WO 03/026589 (3 Apr. 2003); WO 03/026675 (3 Apr. 2003); WO 03/093290 (13 Nov. 2003): US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004).

In one embodiment, nucleoside HCV NS5B polymerase inhibitors that may be combined with the nucleoside derivatives of the present invention are selected from the following compounds: 4'-azido-cytidine; 4-amino-7-(2-C-methyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C,2-O-dimethyl-β-D-ribofuranosyl)-7H-pyrrolo[2,3-a] pyrimidine; and pharmaceutically acceptable salts and prodrugs thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; WO 02/20497 (3 Mar. 2002); WO 2005/016927 (in particular JTK003), assigned to Japan Tobacco, Inc.; the contents of each of which are incorporated herein by reference in their entirety; and HCV-796 (Viropharma Inc.).

In one embodiment, non-nucleoside HCV NS5B polymerase inhibitors that may be combined with the nucleoside derivatives of the present invention are selected from the following compounds: 14-cyclohexyl-6-[2-(dimethylamino) ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5] benzodiazocine-11-carboxylic acid; 14-cyclohexyl-6-[2-(dimethylamino)ethyl]-3-methoxy-5,6,7,8-tetrahydroindolo [2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl] amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5] benzoxazocin-7-yl)-N,N-dimethylethane-1,2-diaminium bis (trifluoroacetate); 14-cyclohexyl-7,8-dihydro-6H-indolo[1, 2-e][1,5]benzoxazocine-11-carboxylic acid; 14-cyclohexyl-6-methyl-7-oxo-5,6,7,8-tetrahydroindolo[2,1-a][2,5] benzodiazocine-11-carboxylic acid; 14-cyclohexyl-3-methoxy-6-methyl-7-oxo-5,6,7,8-tetrahydroindolo[2,1-a][2, 5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5, 6,7,8-tetrahydroindolo[2,1-a][2,5]benzodiazocine-11-carboxylic acid; 14-cyclohexyl-7-oxo-6-(2-piperidin-1-yl-ethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5] benzodiazocine-11-carboxylic acid; 14-cyclohexyl-6-[2-(diethylamino)ethyl]-7-oxo-5,6,7,8-tetrahydroindolo[2,1-a] [2,5]benzodiazocine-11-carboxylic acid; 14-cyclohexyl-6-(1-methylpiperidin-4-yl)-7-oxo-5,6,7,8-tetrahydroindolo[2, 1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5] benzodiazocine-11-carboxamide; 14-cyclohexyl-6-[2-(dimethylamino)ethyl]-N-[(dimethylamino)sulfonyl]-7- oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-a][1,4]benzodiazepine-10-carboxylic acid; and pharmaceutically acceptable salts thereof.

By "pharmaceutically acceptable" is meant that the carrier, diluent, or excipient must be compatible with the other ingredients of the formulation and not deleterious to the recipient thereof.

Also included within the present invention are pharmaceutical compositions comprising the nucleoside aryl phosphoramidates of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Also included within the present invention are pharmaceutical compositions useful for inhibiting RNA-dependent RNA viral polymerase in particular HCV NS5B polymerase comprising an effective amount of a compound of the present invention and a pharmaceutically acceptable carrier. Pharmaceutical compositions useful for treating RNA-dependent RNA viral infection in particular HCV infection are also encompassed by the present invention as well as a method of inhibiting RNA-dependent RNA viral polymerase in particular HCV NS5B polymerase and a method of treating RNA-dependent viral replication and in particular HCV replication. Additionally, the present invention is directed to a pharmaceutical composition comprising a therapeutically effective amount of a compound of the present invention in combination with a therapeutically effective amount of another agent active against RNA-dependent RNA virus and in particular against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), interferon-α2b (such as Intron-A interferon available from Schering Corp., Kenilworth, N.J.), a consensus interferon, and a purified interferon-α product. For a discussion of ribavirin and its activity against HCV, see J. O, Saunders and S. A. Raybuck, "Inosine Monophosphate Dehydrogenase: Consideration of Structure, Kinetics, and Therapeutic Potential," *Ann. Rep. Med. Chem.*, 35: 201-210 (2000).

Another aspect of the present invention provides for the use of the nucleoside aryl phosphoramidates and their pharmaceutical compositions for the manufacture of a medicament for the inhibition of RNA-dependent RNA viral replication, in particular HCV replication, and/or the treatment of RNA-dependent RNA viral infection, in particular HCV infection. Yet a further aspect of the present invention provides for the nucleoside aryl phosphoramidates and their pharmaceutical compositions for use as a medicament for the inhibition of RNA-dependent RNA viral replication, in particular HCV replication, and/or for the treatment of RNA-dependent RNA viral infection, in particular HCV infection.

The pharmaceutical compositions of the present invention comprise a compound of structural formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formula I are administered orally.

For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions are preferably provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The effective dosage of active ingredient employed may vary depending on the particular compound employed, the mode of administration, the condition being treated and the severity of the condition being treated. Such dosage may be ascertained readily by a person skilled in the art. This dosage regimen may be adjusted to provide the optimal therapeutic response.

The compounds of the present invention contain one or more asymmetric centers and can thus occur as racemates and racemic mixtures, single enantiomers, diastereoisomeric mixtures and individual diastereoisomers. When $R^5$ is hydrogen and $R^4$ in the amino acyl residue attached to the phosphorus atom in structural formula I is a substituent other than hydrogen in the formula

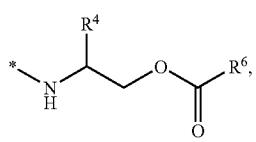

the amino acid residue contains an asymmetric center and is intended to include the individual R- and S-stereoisomers as well as $R^S$-stereoisomeric mixtures. In one embodiment, the stereochemistry at the stereogenic carbon corresponds to that of an S-amino acid, that is, the naturally occurring alpha-amino acid stereochemistry, as depicted in the formula:

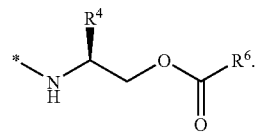

The tetrasubstituted phosphorus in compounds of structural formula I constitutes another asymmetric center, and the compounds of the present invention are intended to encompass both stereochemical configurations at the phosphorus atom.

The present invention is meant to comprehend nucleoside aryl phosphoramidates having the β-D stereochemical configuration for the five-membered furanose ring as depicted in the structural formula below, that is, nucleoside aryl phosphoramidates in which the substituents at C-1 and C-4 of the five-membered furanose ring have the β-stereochemical configuration ("up" orientation as denoted by a bold line).

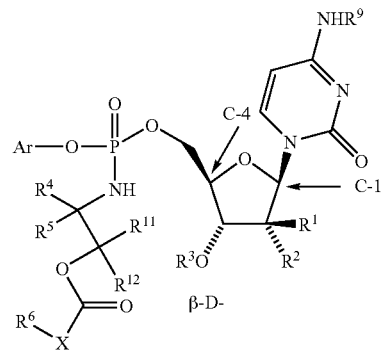

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of structural formula I. Example of keto-enol tautomers which are intended to be encompassed within the compounds of the present invention are illustrated below:

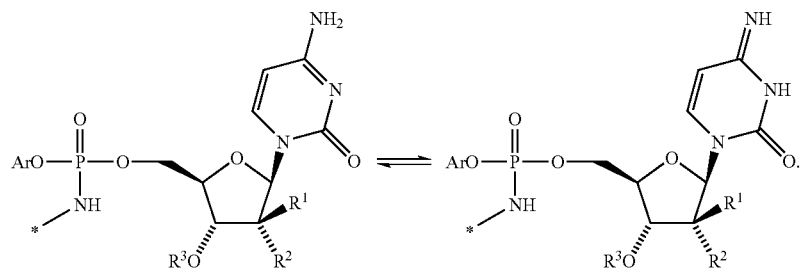

Compounds of structural formula I may be separated into their individual diastereoisomers by, for example, fractional crystallization from a suitable solvent, for example methanol or ethyl acetate or a mixture thereof, or via chiral chromatography using an optically active stationary phase.

Alternatively, any stereoisomer of a compound of the structural formula I may be obtained by stereospecific synthesis using optically pure starting materials or reagents of known configuration.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or hydroxyl group being present in the compounds of the present invention, pharmaceutically acceptable prodrug esters of carboxylic acid derivatives, such as methyl, ethyl, or pivaloyloxymethyl esters or prodrug acyl derivatives of the ribose C-2', C-3', and C-5' hydroxyls, such as O-acetyl, O-pivaloyl, O-benzoyl and O-aminoacyl, can be employed. Included are those esters and acyl groups known in the art for modifying the bioavailability, tissue distribution, solubility, and hydrolysis characteristics for use as sustained-release or prodrug formulations. The contemplated derivatives are readily convertible in vivo into the required compound. Thus, in the methods of treatment of the present invention, the terms "administering" and "administration" is meant to encompass the treatment of the viral infections described with a compound specifically disclosed or with a compound which may not be specifically disclosed, but which converts to the specified compound in vivo after administration to the mammal, including a human patient. Conventional procedures for the selection and preparation of suitable prodrug derivatives are described, for example, in "Design of Prodrugs," ed. H. Bundgaard, Elsevier, 1985, which is incorporated by reference herein in its entirety.

Preparation of the Nucleoside Aryl Phosphoramidates of the Invention:

2'-C-Methylcytidine was prepared as described in the literature by C. Pierra et al., Nucleosides, Nucleotides and Nucleic Acids, 24: 767 (2005) or J. A. Piccirilli et al., J. Org. Chem., 64: 747 (1999). 2'-Deoxy-2'-fluoro-2'-C-methylcytidine is prepared as described in J. Med. Chem., 48: 5504-5508 (2005). The aryl phosphorochloridates for the phosphorylation reactions were prepared according to the methods described in U.S. Pat. No. 6,455,513, the contents of which are incorporated by reference herein in their entirety. The phosphorylation reactions to generate the aryl phosphoroamidates of the present invention were carried out following the methods described in U.S. Pat. No. 6,455,513 and C. McGuigan, et al., J. Med. Chem., 36: 1048 (1993); C. Congiatu, et al., J. Med. Chem., 49: 452-455 (2006); and C. McGuigan, et al., J. Med. Chem., 49: 7215-7226 (2006). For example, phenol or 1-naphthol was reacted with phosphorus oxychloride which was followed by coupling with different amino acid salts to give phenoxy or 1-naphthyloxy phosphorochloridates which were generally purified by flash chromatography and then coupled with the nucleoside in the presence of a suitable base, such as t-butylmagnesium chloride (see M. Uchiyama et al. J. Org. Chem., 58: 373 (1993) and Scheme 1).

General Procedures:

All solvents were obtained from commercial sources and were used without further purification. Reactions were carried out under an atmosphere of nitrogen in oven dried (110° C.) glassware. Organic extracts were dried over sodium sulfate (Na₂SO₄), and were concentrated (after filtration of the drying agent) on rotary evaporators operating under reduced pressure. Flash chromatography was carried out on silica gel following published procedures (W. C. Still et al., J. Org. Chem., 43: 2923 (1978)) or on commercial flash chromatography systems (Biotage corporation and Jones Flashmaster II) utilising pre-packed columns.

Reagents were usually obtained directly from commercial suppliers (and used as supplied) or are readily accessible using routine synthetic steps that are either reported in the scientific literature or are known to those skilled in the art.

$^1$H and $^{31}$P NMR spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a Perkin Elmer API 100, or Waters MicroMass ZQ, operating in negative (ES⁻) or positive (ES⁺) ionization mode and results are reported as the ratio of mass over charge (m/z) for the parent ion only. Preparative scale HPLC separations were carried out on a Waters 2525 pump, equipped with a 2487 dual absorbance detector, on a TSP Spectra system P4000 equipped with a UV1000 absorption module or on a automated, mass-triggered Waters Micromass system incorporating a 2525 pump module, a Micromass ZMD detector and a 2525 collection module. Compounds were eluted with linear gradients of water and MeCN both containing 0.1% trifluoroacetic acid or formic acid using flow rates between 10 and 40 mL/min. Symmetry C18 columns (7 µM, 19×300 mm) were used as stationary phase.

The following abbreviations are used in the examples, the schemes and the tables:
aq.: aqueous; Ar: aryl; atm: atmosphere; CCl₄: carbon tetrachloride; DCM: dichloromethane; DMF: N,N-dimethylformamide; DMSO: dimethylsulfoxide; eq.: equivalent(s); Et₃N: triethylamine; EtOAc: ethyl acetate; Et₂O: diethyl ether; h: hour(s); Me: methyl; MeCN: acetonitrile; MeOH: methanol; min: minutes; MS: mass spectrum; N,N-DMA: N,N,-dimethylacetamide; PE: petroleum ether; Py: pyridine; quant.: quantitative; RP-HPLC: reversed phase high-performance liquid chromatography; RT: room temperature; sec: second(s); TFA: trifluoroacetic acid; and THF: tetrahydrofuran.

The Examples below provide illustrations of the conditions used for the preparation of the compounds of the present invention. These Examples are not intended to be limitations on the scope of the instant invention in any way, and they should not be so construed. Those skilled in the art of nucleoside and nucleotide synthesis will readily appreciate that known variations of the conditions and processes of the following preparative procedures can be used to prepare these and other compounds of the present invention. All temperatures are degrees Celsius unless otherwise noted.

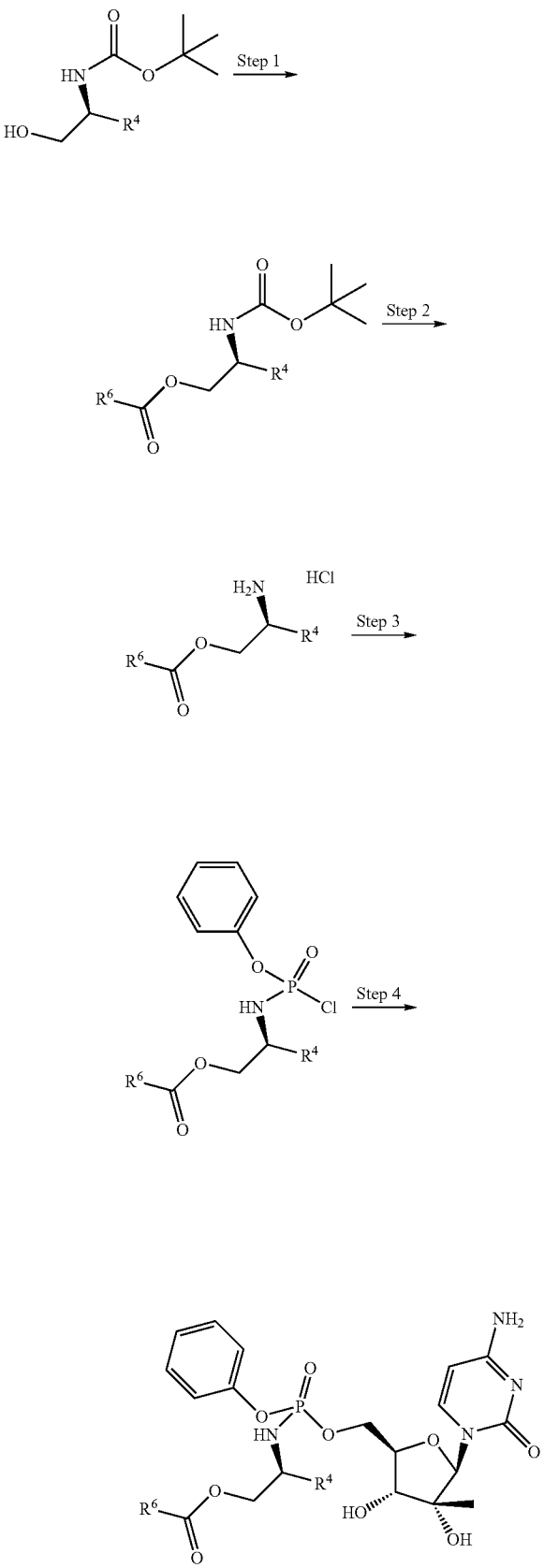

SCHEME 1

Example 1

5'-O—[({(1S)-2-[(2,2-Dimethylpropanoyl)-oxy]-1-methylethyl}-amino)-(phenoxy)-phosphoryl]-2'-C-methylcytidine

Step 1: (2S)-2-[(tert-butoxycarbonyl)-amino]-propyl pivalate

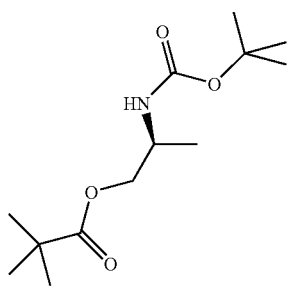

To a solution of the commercially available tert-butyl[(1S)-2-hydroxy-1-methylethyl]carbamate (1.0 eq.) in DCM (0.19M), pivaloyl chloride (1.1 eq.) and Et$_3$N (1.1 eq.) were added. The reaction mixture was stirred at RT for 48 h, then water was added and the organic phase was separated and washed with 10% aqueous citric acid. The residue was purified by column chromatography on silica gel eluting with 92:8 PE/EtOAc.

$^1$H NMR (300 MHz, CDCl$_3$) δ 4.82 (br s, 1H), 4.39-4.25 (m, 3H), 1.75 (s, 9H), 1.55-1.45 (m, 12H)

Step 2: (2S)-2-aminopropyl-2,2-dimethylpropanoate hydrochloride

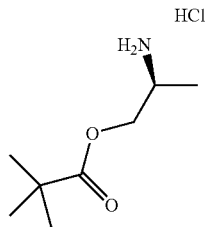

To a solution of (2S)-2-[(tert-butoxycarbonyl)-amino]-propyl pivaloate (1.0 eq.) in EtOAc (0.6 M) was added 4N HCl in dioxane (10 eq.). The reaction mixture was stirred for 2.5 h and then the solvent was evaporated in vacuo to give a solid that was washed with Et$_2$O and dried.

$^1$H NMR (300 MHz, DMSO-d$_6$) δ 8.93 (br s, 3H), 4.62 (dd, J=12.27 and 3.42 Hz, 1H), 4.51 (dd, J=12.27 and 6.74 Hz, 1H), 3.93 (bs, 1H), 1.77 (d, J=6.85 Hz, 3H), 1.57 (s, 9H).

Step 3: (2S)-2-{[chloro(1-phenoxy)phosphoryl]amino}propyl pivaloate

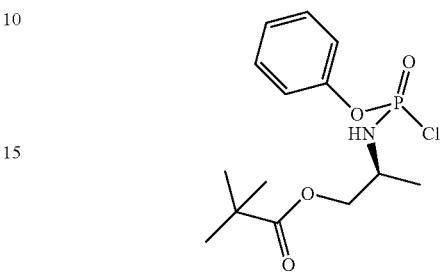

To phenyl dichlorophosphate in DCM (0.12 M) was added (2S)-2-aminopropyl-2,2-dimethylpropanoate hydrochloride (1.0 eq.). After cooling to −78° C., neat Et$_3$N (2.0 eq.) was added and the reaction was left to warm to RT overnight. All volatiles were removed and the resulting white solid was washed with Et$_2$O and filtered. The filtrate was evaporated in vacuo to afford a colourless oil as a 1:1 mixture of diastereoisomers. $^{31}$P NMR (400 MHz, CDCl$_3$): δ 10.08 and 9.92 ppm.

Step 4: 5'-O—[([(1S)-2-[(2,2-dimethylpropanoyl)-oxy]-methylethyl]-amino)-(phenoxy)-phosphoryl]-2'-C-methylcytidine

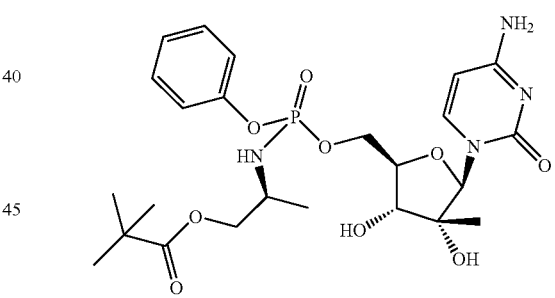

2'-C-Methylcytidine was diluted with THF (0.09 M). The resulting slurry was cooled to −78° C., and tert-butylmagnesium chloride (as 1.0 M solution in THF, 2.2 eq.) was added. The mixture was immediately warmed to 0° C., stirred for 30 min and again cooled to −78° C., then (2S)-2-[[chloro(1-phenoxy)phosphoryl]amino]propyl pivalate (as 1.0 M solution in THF, 2.0 eq.) was added dropwise. The reaction was allowed to reach RT overnight, and then was quenched by the addition of water. The aqueous phase was extracted three times with EtOAc, the combined organic phases were washed with brine and dried over Na$_2$SO$_4$. The crude product was purified by column chromatography on silica gel eluting with 92:8 DCM/MeOH, and the resulting white solid was dissolved in DMSO and purified by RP-HPLC. Fractions containing the pure diastereoisomers were combined and freeze-dried to afford the title compounds as their white TFA salts.

First-Eluting Diastereoisomer:

$^1$H NMR (300 MHz, CD$_3$OD) δ 7.98 (d, J=7.95 Hz, 1H), 7.43-7.20 (m, 5H), 6.02-5.99 (m, 2H), 4.58-4.51 (m, 1H), 4.46-4.37 (m, 1H), 4.22-4.15 (m, 1H), 4.08 (dd, J=10.84, 5.75 Hz, 1H), 3.93 (dd, J=10.72, 6.52 Hz, 1H), 3.77 (d, J=9.29 Hz, 1H), 3.64-3.53 (m, 1H), 1.22 (s, 9H), 1.23-1.17 (m, 6H), NH$_2$, NH, 2×OH not visible, $^{31}$P NMR: (300 MHz CD$_3$OD) δ: 5.56; MS (ES+) m/z 556 (M+H)$^+$ Second-Eluting Diastereoisomer:

$^1$H NMR (300 MHz, CD$_3$OD): δ 8.02 (d, J=7.59 Hz, 1H), 7.44-7.22 (m, 5H), 6.03-6.00 (m, 2H), 4.58-4.53 (m, 1H), 4.43-4.36 (m, 1H), 4.22-4.15 (m, 1H), 4.04 (dd, J=10.94, 5.64 Hz, 1H), 3.91-3.81 (m, 2H), 3.63-3.54 (m, 1H), 1.23-1.17 (m, 15H), NH$_2$, NH, 2×OH not visible, $^{31}$P NMR: (300 MHz CD$_3$OD) δ: 5.68; MS (ES+) m/z 556 (M+H)$^+$ Example 2

5'-O-[{[(±)-2-(Butyryloxy)-1-methylethyl]-amino}-(phenoxy)-phosphoryl]-2'-C-methylcytidine Step 1: (2S)-2-{[chloro(1-phenoxy)phosphoryl]amino}propyl butyrate

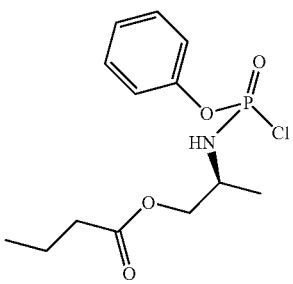

Following the procedure described for Example 1, step 3, treatment of a solution of phenyl dichlorophosphate in DCM (0.144 M) with (2S)-2-aminopropyl butyrate hydrochloride (1.0 eq.), (prepared following the same procedure described for Example 1, step 1 and 2) and Et$_3$N (2.0 eq.) provided the title compound as a colorless oil as a 1:1 mixture of diastereoisomers. $^{31}$P NMR (300 MHz, CDCl$_3$) δ: 10.12 and 9.94.

Step 2: 5'-O-[{[(1S)-2-(butyryloxy)-1-methylethyl]-amino}-(phenoxy)-phosphoryl]-2'-C-methylcytidine

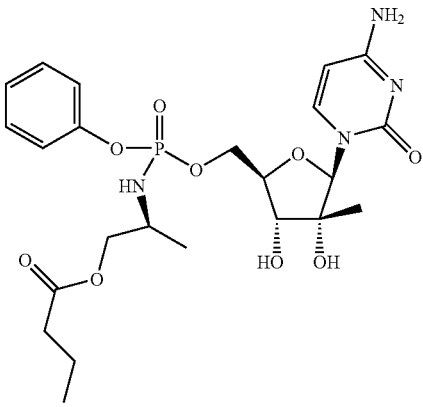

Following the procedure described for Example 1, step 4, 2'-C-methylcytidine in THF (0.097 M) was cooled to −78° C., then tert-butylmagnesium chloride (as 1.0 M solution in THF, 2.2 eq.) was added, followed by the addition of (2S)-2-[[chloro(1-phenoxy)phosphoryl]amino]propyl butyrate (as a 1.0 M solution in THF, 2.0 eq.). The crude was purified by column chromatography on silica gel eluting with 92:8 DCM:MeOH, the resulting solid was dissolved in DMSO and purified by RP-HPLC to afford the title compounds as their TFA salts.

First-Eluting Diastereoisomer:

$^1$H NMR (300 MHz, CD$_3$OD) δ 7.90 (d, J=7.74 Hz, 1H), 7.41-7.23 (m, 5H), 6.03 (s, 1H), 5.97 (d, J=7.08 Hz, 1H), 4.59-4.52 (m, 1H), 4.47-4.36 (m, 1H), 4.18-4.15 (m, 1H), 4.02 (d, J=5.52 Hz, 2H), 3.77 (d, J=9.06 Hz, 1H), 3.63-3.53 (m, 1H), 2.32 (t, J=7.08 Hz, 2H), 1.68-1.60 (m, 2H), 1.17-1.15 (m, 6H), 0.95 (t, J=7.29 Hz, 3H), NH$_2$, NH, 2×OH not visible. $^{31}$P NMR: (300 MHz CD$_3$OD) δ: 5.7; MS (ES+) m/z 542 (M+H)$^+$ Second-Eluting Diastereoisomer:

$^1$H NMR (300 MHz, CD$_3$OD): δ 8.02 (d, J=7.74 Hz, 1H), 7.44-7.22 (m, 5H), 6.01 (s, 1H), 5.98 (d, J=7.98 Hz, 1H), 4.58-4.53 (m, 1H), 4.43-4.36 (m, 1H), 4.21-4.15 (m, 1H), 4.04-3.90 (m, 2H), 3.82 (d, J=9.27 Hz, 1H), 3.63-3.52 (m, 1H), 2.28 (t, J=7.29 Hz, 2H), 1.68-1.56 (m, 2H), 1.21-1.19 (m, 6H), 0.95 (t, J=7.29 Hz, 3H), NH$_2$, NH, 2×OH not visible. $^{31}$P NMR: (300 MHz CD$_3$OD) δ: 5.74; MS (ES+) m/z 542 (M+H)$^+$.

The compounds of the present invention can also be prepared by the procedure depicted in Scheme 2 and exemplified by Example 3.

SCHEME 2

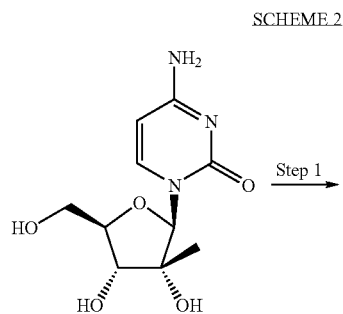

Step 1 →

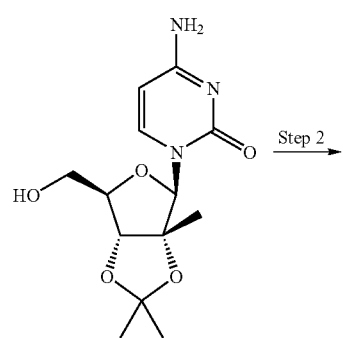

Step 2 →

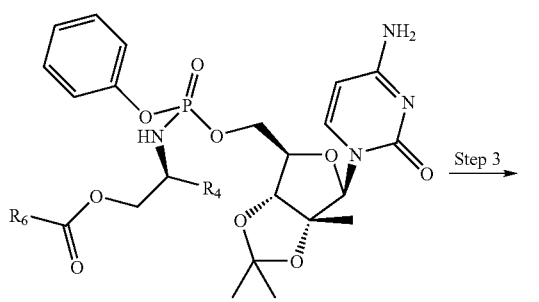

Step 3 →

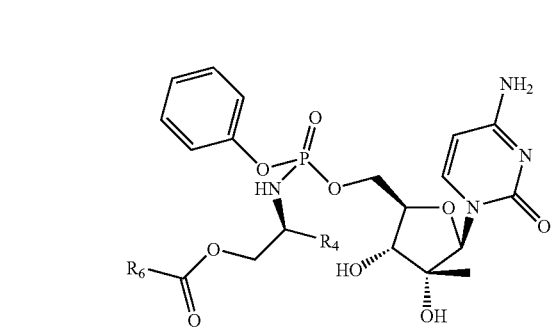

Example 3

5'-O-[[[2-(2,2-Dimethyl-1-oxopropoxy)-ethyl]-amino]-(phenoxy)-phosphinyl]-2'-C-methylcytidine Step 1: 2'-C-methyl-2',3'-O-(1-methylethylidene)-cytidine

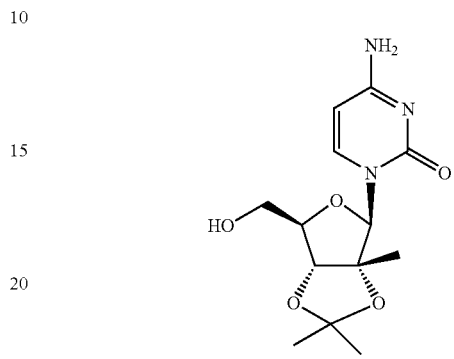

2'-C-Methylcytidine was diluted with acetone (0.04M) and p-toluensulfonic acid and 2,2-dimethoxypropane were added. The resulting slurry was stirred for 24 h at RT. The solvent was evaporated, the residue was dissolved in MeOH and Amberlite A-26 (previously washed with 2N NaOH and H$_2$O) was added. The resulting mixture was stirred for 2 h. The Amberlite was filtered off and the solution was evaporated. The crude product was purified by column chromatography on silica gel (DCM/MeOH=9:1) to give the desired product as a white powder.

$^1$H NMR (300 MHz, CD$_3$OD) δ 7.96 (d, J=7.56 Hz, 1H), 6.18 (s, 1H), 5.90 (d, J=7.56 Hz, 1H), 4.51-4.48 (m, 1H), 4.28-4.23 (m, 1H), 3.86 (dd, J=3.04 and 12.12 Hz, 1H), 3.78 (dd, J=3.52 and 12.12 Hz, 1H), 1.59 (s, 3H), 1.43 (s, 3H), 1.25 (s, 3H); MS (ES+) m/z 298 (M+H)$^+$ Step 2: 5'-O-[[[2-(2,2-dimethyl-1-oxopropoxy)-ethyl]-amino]-phenoxyphosphinlyl]-2'-C-methyl-2', 3'-O-(1-methylethylidene)-cytidine

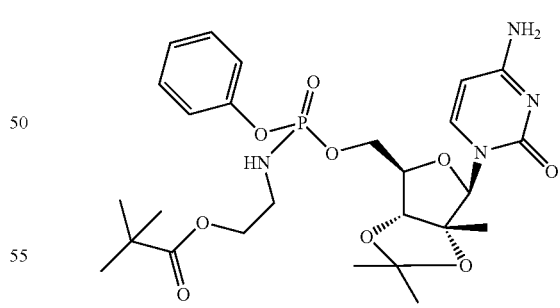

2'-C-Methyl-2',3'-O-(1-methylethylidene)-cytidine was diluted with pyridine (0.67M) in presence of molecular sieves. The resulting solution was cooled to 0° C., diphenylphosphite (80%, 2.0 eq.) was added, and the mixture was stirred for 1 h at 0° C. The solvent was evaporated and the residue dissolved in THF (0.08M). The resulting solution was cooled to 0° C. and Et$_3$N (6.0 eq.), hexachloroethane (0.8 M in DCM) and aminoethyl-2,2-dimethylpropanoate hydrochloride (prepared as described in Example 1, Step 2) were added. The mixture was stirred for 30 min at 0° C. and then was quenched by the addition of water. The aqueous phase was extracted three times with EtOAc, the combined organic phases were washed with brine and dried over Na₂SO₄. The crude product was purified by column chromatography on silica gel (DCM/MeOH=95:5) to give a white solid as mixture of diastereoisomers. MS (ES+) m/z 581 (M+H)⁺

Step 3: 5'-O-[[[2-(2,2-dimethyl-1-oxopropoxy)-ethyl]-amino]-(phenoxy)-phosphinyl]-2'-C-methyl-cytidine

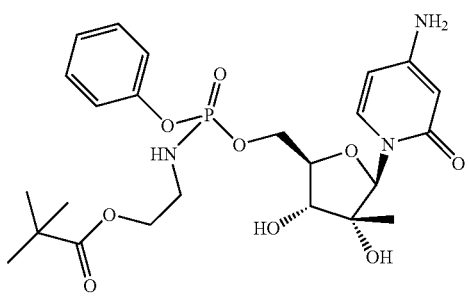

5'-O-[[[2-(2,2-Dimethyl-1-oxopropoxy)-ethyl]-amino]-phenoxyphosphinyl]-2'-C-methyl-2',3'-O-(1-methylethylidene)-cytidine was dissolved in a solution of TFA-H₂O (8:2, 0.098M). The resulting solution was warmed to 30° C. and stirred for 20 min. The solvent was evaporated and the residue was dissolved in acetonitrile and purified by RP-HPLC (stationary phase: column Phenomenex-Luna C₁₈, 5 μm, 21.20×250 mm. Mobile phase: acetonitrile/H₂O 5 mM AMBIC). Fractions containing the pure diastereoisomers were combined and freeze-dried to afford the title compounds as white powders.

First-Eluting Diastereoisomer:

¹H NMR (300 MHz, DMSO-d₆) δ 7.57 (d, J=7.26 Hz, 1H), 7.44-7.38 (m, 2H), 7.26-7.12 (m, 5H), 5.96 (s, 1H), 5.78-5.68 (m, 2H), 5.33 (d, J=6.87 Hz, 1H), 5.1 (s, 1H), 4.4-4.15 (m, 2H), 4.08-3.92 (m, 3H), 3.99-3.58 (m, 1H), 3.17-3.05 (m, 2H), 1.15 (s, 9H), 0.96 (s, 3H); ³¹P NMR: (300 MHz DMSO-d₆) δ: 5.42; MS (ES+) m/z 541 (M+H)⁺

Second-Eluting Diastereoisomer:

¹H NMR (400 MHz, DMSO-d₆) δ 7.57 (d, J=7.32 Hz, 1H), 7.44-7.39 (m, 2H), 7.26-7.10 (m, 5H), 5.96 (br s, 1H), 5.70-5.65 (m, 2H), 5.31 (d, J=7.08 Hz, 1H), 5.13 (s, 1H), 4.42-4.24 (m, 2H), 4.09-3.92 (m, 3H), 3.68-3.56 (m, 1H), 3.12-3.05 (m, 2H), 1.15 (s, 9H), 0.98 (s, 3H); ³¹P NMR: (400 MHz DMSO-d₆) δ: 5.68; MS (ES+) m/z 541 (M+H)⁺

Example 4

5'-O-[[[2-(2-Methyl-1-oxopropoxy)ethyl]-amino]-(phenoxy)-phosphinyl]-2'-C-methylcytidine

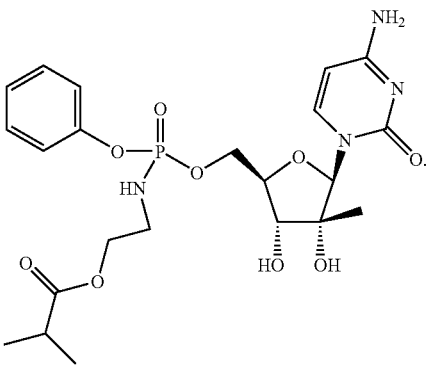

Following the procedure described for Example 3, Step 2 [starting from 2'-C-methyl-2',3'-O-(1-methylethylidene)-cytidine (prepared as described in Example 3, Step 1) and aminoethyl-2-methylpropanoate hydrochloride (prepared as described in Example 1, Step 2)] and Step 3, there was obtained a crude product that was purified by RP-HPLC (stationary phase: column Phenomenex-Luna C₁₈, 5 μm, 21.20×250 mm. Mobile phase: acetonitrile/H₂O 5 mM AMBIC). Fractions containing the pure compound were combined and freeze-dried to afford the title compound as a white powder.

First-Eluting Diastereoisomer:

¹H NMR (400 MHz, CD₃OD) δ 7.71 (d, J=7.74 Hz, 1H), 7.43-7.38 (m, 2H), 7.29 (d, J=8.5 Hz, 2H), 7.23 (t, J=7.3 Hz, 1H), 6.01 (s, 1H), 5.84 (d, J=7.56 Hz, 1H), 4.56-4.37 (m, 2H), 4.15-4.08 (m, 3H), 3.76 (d, J=9.12 Hz, 1H), 3.30-3.23 (m, 2H), 2.61-2.53 (m, 1H), 1.15 (d, J=6.72 Hz, 6H), 1.11 (s, 3H). ³¹P NMR: (400 MHz CD₃OD) δ: 5.67; MS (ES+) m/z 527 (M+H)⁺

Second-Eluting Diastereoisomer:

¹H NMR (400 MHz, CD₃OD) δ 7.74 (d, J=7.74 Hz, 1H), 7.44-7.39 (m, 2H), 7.3-7.24 (m, 3H), 6.07 (s, 1H), 5.83 (d, J=7.6 Hz, 1H), 4.57-4.52 (m, 1H), 4.42-4.36 (m, 1H), 4.15-4.08 (m, 3H), 3.78 (d, J=9.08 Hz, 1H), 3.30-3.23 (m, 2H), 2.59-2.52 (m, 1H), 1.16-1.11 (m, 9H). $^{31}$P NMR: (400 MHz CD$_3$OD) δ: 5.74; MS (ES+) m/z 527 (M+H)$^+$

Example 5

5'-O-[{[(1S)-1-Methyl-2-(2-methyl-1-oxopropoxy)ethyl]-amino}-(phenoxy)-phosphinyl]-2'-C-methyl-cytidine

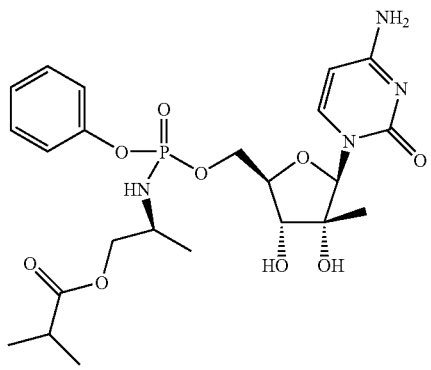

Following the procedure described for Example 3, Steps 2 and 3, there was obtained a crude product that was purified by RP-HPLC (stationary phase: column Phenomenex-Luna C$_{18}$, 5 μm, 21.20×250 mm. Mobile phase: acetonitrile/H$_2$O 5 mM AMBIC). Fractions containing the pure compound were combined and freeze-dried to afford the title compound as a white powder.

First-Eluting Diastereoisomer:

$^1$H NMR (300 MHz, CD$_3$OD) δ 7.71 (d, J=7.44 Hz, 1H), 7.45-7.28 (m, 2H), 7.31-7.19 (m, 3H), 6.07 (s, 1H), 5.85 (d, J=7.44 Hz, 1H), 4.56-4.4.51 (m, 1H), 4.43-4.38 (m, 1H), 4.15-4.10 (m, 1H), 4.06-3.96 (m, 2H), 3.73 (d, J=9.24 Hz, 1H), 3.64-3.54 (m, 1H), 2.63-2.53 (m, 1H), 1.18-1.15 (m, 9H), 1.10 (s, 3H). $^{31}$P NMR: (300 MHz CD$_3$OD) δ: 4.46; MS (ES+) m/z 541 (M+H)$^+$

Second-Eluting Diastereoisomer:

$^1$H NMR (300 MHz, CD$_3$OD) δ 7.73 (d, J=7.44 Hz, 1H), 7.43-7.38 (m, 2H), 7.30-7.23 (m, 3H), 6.07 (s, 1H), 5.83 (d, J=7.44 Hz, 1H), 4.57-4.51 (m, 1H), 4.42-4.35 (m, 1H), 4.15-4.11 (m, 1H), 4.04-3.90 (m, 2H), 3.79 (d, J=9.27 Hz, 1H), 3.66-3.57 (m, 1H), 2.60-2.50 (m, 1H), 1.20 (d, J=6.66 Hz, 3H), 1.16-1.13 (m, 9H). $^{31}$P NMR: (300 MHz CD$_3$OD) δ: 4.51; MS (ES+) m/z 541 (M+H)$^+$

Example 6

5'-O-[{[(1S,2S)-1-[(2,2-Dimethyl-1-oxopropoxy)methyl]-2-methylbutyl]amino}-(phenoxy)-phosphoryl]-2'-C-methylcytidine

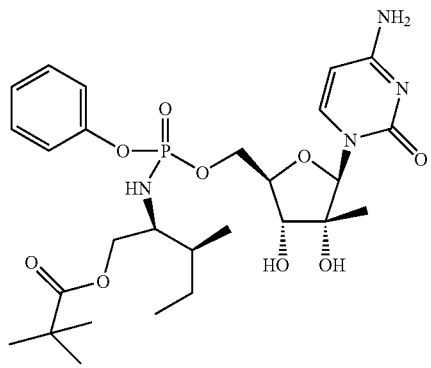

Following the procedure described for Example 3, Step 2 and 3, there was obtained a crude product that was purified by RP-HPLC (stationary phase: column Phenomenex-Luna C$_{18}$, 5 μm, 21.20×250 mm. Mobile phase: acetonitrile/H$_2$O 5 mM AMBIC). Fractions containing the pure compound were combined and freeze-dried to afford the title compound as a white powder.

First-Eluting Diastereoisomer:

$^1$H NMR (300 MHz, CD$_3$OD) δ 7.70 (d, J=7.44 Hz, 1H), 7.43-7.37 (m, 2H), 7.30-7.20 (m, 3H), 6.07 (s, 1H), 5.82 (d, J=7.44 Hz, 1H), 4.54 (dd, J=3.63 and 11.46 Hz, 1H), 4.42-4.35 (m, 1H), 4.14-3.99 (m, 3H), 3.77 (d, J=9.06 Hz, 1H), 3.47-3.37 (m, 1H), 1.71-1.52 (m, 2H), 1.25-1.1 (m, 1H), 1.19 (s, 9H), 1.12 (s, 3H), 0.98-0.9 (m, 6H), NH$_2$, NH, 2×OH not visible. $^{31}$P NMR: (300 MHz CD$_3$OD) δ: 5.02; MS (ES+) m/z 598 (M+H)$^+$ Second-Eluting Diastereoisomer:

$^1$H NMR (400 MHz, CD$_3$OD) δ 7.66 (d, J=7.56 Hz, 1H), 7.41-7.37 (m, 2H), 7.21-7.20 (m, 3H), 6.06 (s, 1H), 5.84 (d, J=7.56 Hz, 1H), 4.55-4.49 (m, 1H), 4.42-4.37 (m, 1H), 4.23-4.19 (m, 1H), 4.13-4.05 (m, 2H), 3.70 (d, J=9.32 Hz, 1H), 3.44-3.37 (m, 1H), 1.59-1.50 (m, 2H), 1.23 (s, 9H), 1.23-1.12 (m, 1H), 1.08 (s, 3H), 0.92-0.86 (m, 6H), NH$_2$, NH, 2×OH not visible. $^{31}$P NMR: (400 MHz CD$_3$OD) δ: 4.91; MS (ES+) m/z 598 (M+H)$^+$ The following additional Examples (see Table 1) were prepared following the procedures detailed above for Example 3.

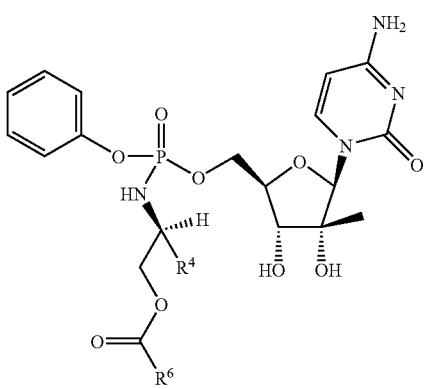

TABLE 1

| Ex. | R⁴ | R⁶ | Chemical name | MS (M + 1) |
|---|---|---|---|---|
| 7 | n-Bu | t-Bu | 5'-O-[[[(1S)-1-[(2,2-dimethyl-1-oxopropoxy)methyl]pentyl]amino]-(phenoxy)-phosphinyl]-2'-C-methylcytidine | 597 |
| 8 | Bn | t-Bu | 5'-O-[[[(1S)-2-[(2,-dimethyl-1-oxopropoxy)-1-(phenylmethyl)]-ethyl]amino]-(phenoxy)-phosphinyl]-2'-C-methylcytidine | 631 |

Example 9

5'-O-[[[2-[(1-oxo-2-propylpentyl) oxy]ethyl]amino]phenoxyphosphinyl]-2'-C-methylcytidine

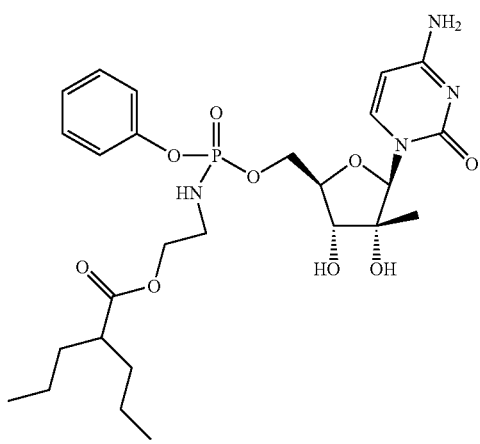

Following the procedure described for Example 3, Steps 2 and 3 [starting from 2'-C-methyl-2',3'-O-(1-methylethylidene)-cytidine (prepared as described in Example 3, Step 1) and aminoethyl-2-propylpentanoate hydrochloride a crude product was obtained that was purified by RP-HPLC (stationary phase: column Phenomenex-Luna C18, 5 μm, 21.20×250 mm. Mobile phase: acetonitrile/H₂O 5 mM AMBIC). Fractions containing the pure compounds were combined and freeze-dried to afford the title compound as a white powder.
First-Eluting Diastereoisomer:

¹H NMR (300 MHz, CD₃OD) δ 7.71 (d, J=7.6 Hz, 1H), 7.43-7.19 (m, 5H), 6.07 (s, 1H), 5.83 (d, J=6.8 Hz, 1H), 4.58-4.5 (m, 1H), 4.47-4.34 (m, 1H), 4.18-4.05 (m, 3H), 3.74 (d, J=9.1 Hz, 1H), 3.35-3.2 (m, 2H), 2.48-2.33 (m, 1H), 1.66-1.37 (m, 4H), 1.37-1.23 (m, 4H), 1.1 (s, 3H), 0.95-0.86 (m, 6H). ³¹P NMR: (300 MHz CD₃OD) δ: 5.45; MS (ES+) m/z 583 (M+H)⁺
Second-Eluting Diastereoisomer:

¹H NMR (300 MHz, CD₃OD) δ 7.71 (d, J=7.4 Hz, 1H), 7.46-7.37 (m, 2H), 7.33-7.21 (m, 3H), 6.05 (s, 1H), 5.81 (d, J=7.3 Hz, 1H), 4.56-4.50 (m, 1H), 4.44-4.34 (m, 1H), 4.18-4.05 (m, 3H), 3.76 (d, J=9.1 Hz, 1H), 3.35-3.20 (m, 2H), 2.46-2.35 (m, 1H), 1.66-1.37 (m, 4H), 1.37-1.22 (m, 4H), 1.12 (s, 3H), 0.97-0.86 (m, 6H). ³¹P NMR: (300 MHz CD₃OD) δ: 5.52; MS (ES+) m/z 583 (M+H)⁺

Example 10

5'-O-[[[(1S)-2-(1H-indol-3-yl)-1-(2-methyl-1-oxopropoxy)methyl]ethyl]amino]phenoxyphosphinyl]-2'-C-methylcytidine

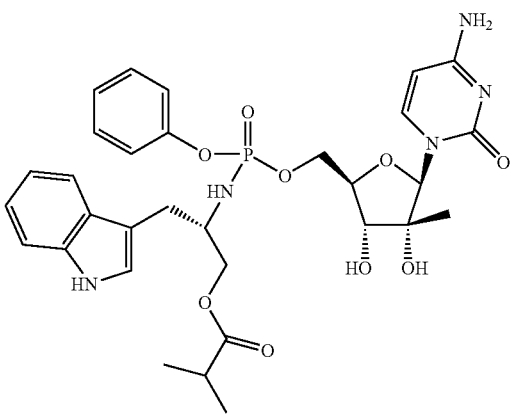

Following the procedure described for Example 3, Steps 2 and 3 [starting from 2'-C-methyl-2',3'-O-(1-methylethylidene)-cytidine (prepared as described in Example 3, Step 1) and (2S)-2-amino-3-(1H-indol-3-yl) propyl 2-methylpropanoate hydrochloride a crude product was obtained that was purified by RP-HPLC (stationary phase: column Phenomenex-Luna C18, 5 μm, 21.20×250 mm. Mobile phase: acetonitrile/H₂O 5 mM AMBIC). Fractions containing the pure compounds were combined and freeze-dried to afford the title compound as a white powder.
First-Eluting Diastereoisomer:

¹H NMR (300 MHz, CD₃OD) δ 7.57 (d, J=7.5 Hz, 1H), 7.51 (d, J=7.7 Hz, 1H), 7.36-7.30 (m, 3H), 7.21-7.04 (m, 5H), 6.99-6.93 (m, 1H), 6.00 (s, 1H), 5.78 (d, J=7.47 Hz, 1H), 4.28-4.10 (m, 4H), 3.98-3.94 (m, 1H), 3.84-3.77 (m, 1H), 3.60 (d, J=9.3 Hz, 1H), 3.1-2.89 (m, 2H), 2.63-2.56 (m, 1H), 1.18 (d, J=7.0 Hz, 6H), 1.03 (s, 3H). ³¹P NMR: (300 MHz CD₃OD) δ: 4.18; MS (ES+) m/z 656 (M+H)⁺
Second-Eluting Diastereoisomer:

¹H NMR (300 MHz, CD₃OD) δ 7.6 (d, J=7.3 Hz, 1H), 7.54 (d, J=7.9 Hz, 1H), 7.4-7.33 (m, 3H), 7.23-7.18 (m, 3H), 7.11-6.97 (m, 3H), 6.02 (s, 1H), 5.71 (d, J=7.3 Hz, 1H), 4.32-4.24 (m, 1H), 4.11-4.0 (m, 4H), 3.99-3.82 (m, 1H), 3.68 (d, J=9.1 Hz, 1H), 3.1-2.95 (m, 2H), 2.61-2.51 (m, 1H), 1.16 (d, J=6.9 Hz, 6H), 1.08 (s, 3H). ³¹P NMR: (300 MHz CD₃OD) δ: 4.43; MS (ES+) m/z 656 (M+H)⁺

Example 11

5'-O-[[[(1S)-2-(2-methyl-1-oxopropoxy)-1-(phenylmethyl)ethyl]amino]phenoxyphosphinyl]-2'-C-methylcytidine

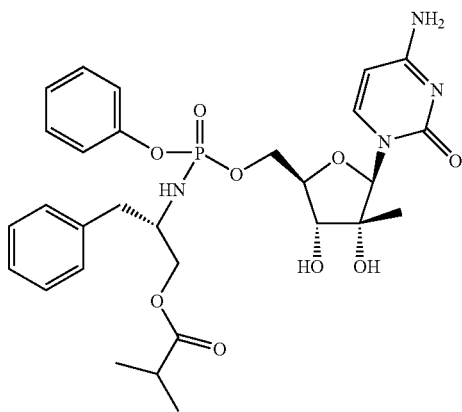

Following the procedure described for Example 3, Steps 2 and 3 [starting from 2'-C-methyl-2',3'-O-(1-methylethylidene)-cytidine (prepared as described in Example 3, Step 1) and (2S)-2-amino-3-phenylpropyl 2-methylpropanoate hydrochloride a crude product was obtained that was purified by RP-HPLC (stationary phase: column Symmetry C18, 5 μm, 19×300 mm. Mobile phase: acetonitrile/$H_2O$ 0.1% TFA). Fractions containing the pure compounds were combined and freeze-dried to afford the title compound as a white powder.

First-Eluting Diastereoisomer:

$^1$H NMR (300 MHz, DMSO-$d_6$) δ 9.18 (s br, 1H), 8.31 (s br, 1H), 7.77 (d, J=7.5 Hz, 1H), 7.38-7.13 (m, 10H), 5.90 (d, J=7.5 Hz, 1H), 5.8 (s, 11H), 5.69 (t, J=11.3 Hz, 1H), 4.19-4.0 (m, 2H), 3.99-3.92 (m, 1H), 3.86-3.79 (m, 2H), 3.57-3.5 (m, 2H), 2.8-2.65 (m, 2H), 2.54-2.41 (m, 1H), 1.05 (d, J=6.8 Hz, 6H), 1.0 (s, 3H). $^{31}$P NMR: (300 MHz, d6-DMSO) δ: 4.41; MS (ES+) m/z 617 (M+H)$^+$

Second-Eluting Diastereoisomer:

$^1$H NMR (300 MHz, DMSO-$d_6$) δ 9.12 (s br, 1H), 8.31 (s br, 1H), 7.77 (d, J=7.7 Hz, 1H), 7.34-7.07 (m, 10H), 5.92 (d, J=7.7 Hz, 1H), 5.83 (s, 1H), 5.75 (t, J=11.3 Hz, 1H), 4.23-4.4 (m, 2H), 4.2-3.85 (m, 3H), 3.59-3.47 (m, 2H), 2.81-2.61 (m, 2H), 2.54-2.42 (m, 1H), 1.06 (d, J=6.8 Hz, 6H), 0.99 (s, 3H). $^{31}$P NMR: (300 MHz, d6-DMSO) δ: 4.05; MS (ES+) m/z 617 (M+H)$^+$

Example 12

5'-O-[[[(2S)-2-(2-methyl-1-oxopropoxy) propyl]amino]phenoxyphosphinyl]-2'-C-methylcytidine

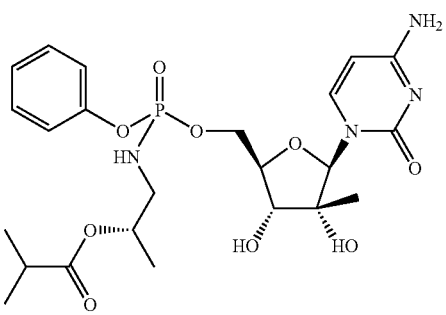

Following the procedure described for Example 3, Steps 2 and 3 [starting from 2'-C-methyl-2',3'-O-(1-methylethylidene)-cytidine (prepared as described in Example 3, Step 1) and (1S)-2-amino-1-methylethyl 2-methylpropanoate hydrochloride a crude product was obtained that was purified by RP-HPLC (stationary phase: column X-Terra C18, 5 μm, 50×100 mm. Mobile phase: acetonitrile/$H_2O$ 0.05% TFA). Fractions containing the pure compounds were combined and freeze-dried to afford the title compound as a white powder.

First-Eluting Diastereoisomer:

$^1$H NMR (400 MHz, DMSO-$d_6$) δ 9.62 (bs, 1H), 8.86 (bs, 1H), 7.89 (d, J=7.6 Hz, 1H), 7.45-7.09 (m, 5H), 6.02 (d, J=7.6 Hz, 1H), 5.80 (s, 1H), 5.71-5.54 (m, 1H), 4.45-4.18 (m, 2H), 4.12-3.98 (m, 1H), 3.95-3.73 (m, 2H), 3.66-3.53 (m, 1H), 3.48-3.28 (m, 1H), 1.10-0.95 (m, 12H). $^{31}$P NMR: (400 MHz, DMSO) δ: 4.49; MS (ES+) m/z 541 (M+H)$^+$

Second-Eluting Diastereoisomer:

$^1$H NMR (400 MHz, DMSO-$d_6$) δ 9.63 (bs, 1H), 8.84 (bs, 1H), 7.92 (d, J=7.6 Hz, 1H), 7.55-7.15 (m, 5H), 6.02 (d, J=7.6 Hz, 1H), 5.82 (s, 1H), 5.70-5.55 (m, 1H), 4.45-4.20 (m, 2H), 4.12-4.00 (m, 1H), 3.95-3.75 (m, 2H), 3.66-3.55 (m, 1H), 3.48-3.28 (m, 1H), 1.10-0.95 (m, 12H). $^{31}$P NMR: (400 MHz, DMSO) δ: 4.67; MS (ES+) m/z 541 (M+H)$^+$

Example 13

5'-O-[[[(2R)-2-(2-methyl-1-oxopropoxy) propyl]amino]phenoxyphosphinyl]-2'-C-methylcytidine

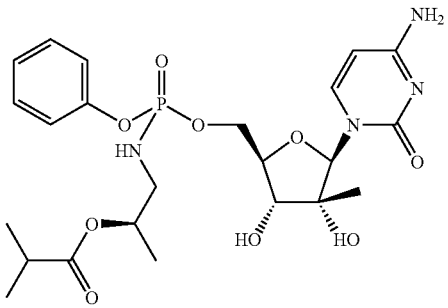

Following the procedure described for Example 3, Steps 2 and 3 [starting from 2'-C-methyl-2',3'-O-(1-methylethylidene)-cytidine (prepared as described in Example 3, Step 1) and (1R)-2-amino-1-methylethyl 2-methylpropanoate hydrochloride a crude product was obtained that was purified by RP-HPLC (stationary phase: column X-Terra C$_{18}$, 5 μm, 50×100 mm. Mobile phase: acetonitrile/H$_2$O 5 mM AMBIC). Fractions containing the pure compounds were combined and freeze-dried to afford the title compound as a white powder.

First-Eluting Diastereoisomer:
$^1$H NMR (400 MHz, DMSO-d$_6$) δ 8.20-70.80 (m, 1H), 7.50-7.02 (m, 5H), 6.15-5.93 (m, 1H), 5.83 (m, 1H), 4.51-4.17 (m, 2H), 4.17-3.97 (m, 1H), 3.97-3.70 (m, 2H), 3.69-3.52 (m, 1H), 3.49-3.33 (m, 1H), 1.16-0.93 (m, 12H). $^{31}$P NMR: (400 MHz, DMSO) δ: 4.33; MS (ES+) m/z 541 (M+H)$^+$ Second-Eluting Diastereoisomer:
$^1$H NMR (400 MHz, DMSO-d$_6$) δ 7.89 (d, J=7.6 Hz, 1H), 7.34-7.00 (m, 5H), 5.97 (d, J=7.6 Hz, 1H), 5.83 (s, 1H), 4.45-4.32 (m, 1H), 4.32-4.18 (m, 1H), 4.07-3.97 (m, 1H), 3.92-3.70 (m, 2H), 3.70-3.58 (m, 1H), 3.48-3.31 (m, 1H), 1H hidden by DMSO, 1.09-0.87 (m, 12H). $^{31}$P NMR: (400 MHz, DMSO) δ: 4.48; MS (ES+) m/z 541 (M+H)$^+$

Examples 14-21

The compounds of Examples 14 and 15 were prepared according to the procedure set forth in steps 1 and 2 of Scheme 2 and exemplified in steps 1 and 2 of Example 3. The compounds of Examples 16-21 were prepared according to the procedure set forth in Scheme 2 and exemplified in Example 3 above.

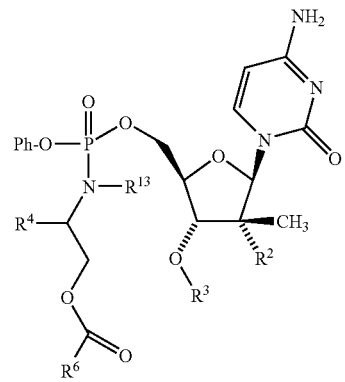

TABLE 2

| Ex. | Chemical name | R$^2$ | R$^3$ | R$^4$ | R$^6$ | R$^{13}$ | MS (M + 1) |
|---|---|---|---|---|---|---|---|
| 14 | cytidine, 5'-O-[[[(1S)-2-(2,2-dimethyl-1-oxopropoxy)-1-(phenylmethyl)ethyl]amino]phenoxyphosphinyl]-2'-C-methyl-2',3'-O-(1-methylethylidene)- | R$^2$ + R$^3$ = 2',3'-Acetonide | | Bn | t-Bu | H | 671 |
| 15 | cytidine, 5'-O-[[[(1S)-1-[(2,2-dimethyl-1-oxopropoxy)methyl]pentyl]amino]phenoxyphosphinyl]-2'-C-methyl-2',3'-O-(1-methylethylidene)- | R$^2$ + R$^3$ = 2',3'-Acetonide | | n-Bu | t-Bu | H | 637 |
| 16 | cytidine, 5'-O-[[[2-(benzoyloxy)ethyl]amino]phenoxyphosphinyl]-2'-C-methyl- | OH | H | H | Ph | H | 561 |
| 17 | 5'-O-[({(1S)-1-benzyl-2-[(2,2-dimethylpropanoyl)oxy]ethyl}amino)(phenoxy)phosphoryl]-2'-C-methylcytidine | OH | H | Bn | t-Bu | H | 631 |
| 18 | 5'-O-[{[2-(acetyloxy)ethyl]amino}(phenoxy)phosphoryl]-2'-C-methylcytidine | OH | H | H | Me | H | 499 |
| 19 | cytidine, 2'-C-methyl-5'-O-[[methyl[2-(2-methyl-1-oxopropoxy)ethyl]amino]phenoxyphosphinyl]- | OH | H | H | i-Pr | Me | 541 |
| 20 | 5'-O-[({2-[(2-ethylbutanoyl)oxy]ethyl}amino)(phenoxy)phosphoryl]-2'-C-methylcytidine | OH | H | H | 3-Pen | H | 555 |
| 21 | 5'-O-[({2-[(cycloheptylcarbonyl)oxy]ethyl}amino)(phenoxy)phosphoryl]-2'-C-methylcytidine | OH | H | H | cycloheptyl | H | 581 |

Ph = phenyl,
Bn = benzyl,
t-Bu = tert-butyl,
i-Pr = isopropyl,
3-Pen = 3-pentyl,
Me = methyl

Example 22

2'-C-methyl-5'-O-[[(3R)-3-(2-methyl-1-oxopropoxy)-1-pyrrolidinyl]phenoxyphosphinyl]-cytidine

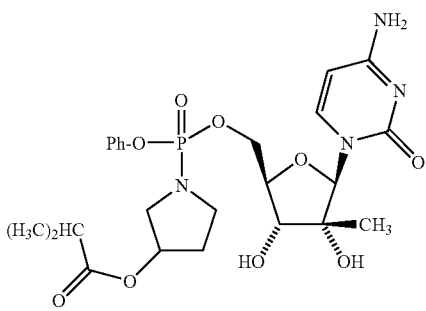

The title compound was prepared according to the procedure set forth in Scheme 2 and exemplified in Example 3, wherein pyrrolidiny-3-yl-2-methyl propanoate hydrochloride was used in place of aminoethyl-2,2-dimethyl propanoate hydrochloride. MS (M+1)=553.

Biological Assays:

The assay employed to measure the inhibition of HCV replication is described below.

A. Assay for Inhibition of HCV RNA Replication:

The compounds of the present invention are evaluated for their ability to affect the replication of Hepatitis C Virus RNA in cultured hepatoma (HuH-7) cells containing a subgenomic HCV Replicon. The details of the assay are described below. This Replicon assay is a modification of that described in V. Lohmann, F. Korner, J-O. Koch, U. Herian, L. Theilmann, and R. Bartenschlager, "Replication of a Sub-genomic Hepatitis C Virus RNAs in a Hepatoma Cell Line," *Science* 285: 110 (1999).

Protocol:

The assay is an in situ Ribonuclease protection, Scintillation Proximity based-plate assay (SPA). 10,000-40,000 cells are plated in 100-200 µL of media containing 0.8 mg/mL G418 in 96-well cytostar plates (Amersham). Compounds are added to cells at various concentrations up to 100 µM in 1% DMSO at time 0 to 18 h and then cultured for 24-96 h. Cells are fixed (20 min, 10% formalin), permeabilized (20 min, 0.25% Triton X-100/PBS) and hybridized (overnight, 50° C.) with a single-stranded $^{33}$P RNA probe complementary to the (+) strand NS5B (or other genes) contained in the RNA viral genome. Cells are washed, treated with RNAse, washed, heated to 65° C. and counted in a Top-Count. Inhibition of replication is read as a decrease in counts per minute (cpm).

Human HuH-7 hepatoma cells, which are selected to contain a subgenomic replicon, carry a cytoplasmic RNA consisting of an HCV 5' non-translated region (NTR), a neomycin selectable marker, an EMCV IRES (internal ribosome entry site), and HCV non-structural proteins NS3 through NS5B, followed by the 3' NTR.

Representative compounds tested in the replication assay exhibit $EC_{50}$'s less than 100 micromolar. For example, the title compounds of Examples 1-22 were tested in the replicon assay and were found to have $EC_{50}$ values as set forth in Table 3 below.

TABLE 3

| Example No. | Replicon Assay $EC_{50}$ (µM)[a] |
|---|---|
| 1 | 1.6/0.9 |
| 2 | 2.8/4.0 |
| 3 | >5.0/0.2 |
| 4 | 2.0/0.2 |
| 5 | 0.9/0.5 |
| 6 | 2.0/1.8 |
| 7 | 1.5/0.7 |
| 8 | 1.0[b] |
| 9 | 0.5/0.2 |
| 10 | 0.2/0.7 |
| 11 | 0.5/0.9 |
| 12 | 2.2/2.4 |
| 13 | 0.5/1.7 |
| 14 | >5.0/>5.0 |
| 15 | >10[b] |
| 16 | 2.2/5.0 |
| 17 | 1.4/0.1 |
| 18 | 2.4/1.3 |
| 19 | >5.0/>5.0 |
| 20 | 2.8/0.6 |
| 21 | 0.7/1.2 |
| 22 | >5.0/>5.0 |

[a]Values refer to first and second eluting diastereomers, respectively.
[b]Mixture of diastereomers was tested.

B. Assay for Intracellular Metabolism:

Part One

The compounds of the present invention can also be evaluated for their ability to enter a human hepatoma cell line and be converted intracellularly into the corresponding nucleoside 5'-mono-, di-, and triphosphates.

Two cell lines, HuH-7 and HBI10A, are used for intracellular metabolism studies of the compounds of the present invention. HuH-7 is a human hepatoma cell line, and HBI10A denotes a clonal line derived from HuH-7 cells that harbors the HCV bicistronic replicon. HuH-7 cells are plated in complete Dulbecco's modified Eagle's medium containing 10% fetal bovine serum and HBI10A cells in the same containing G418 (0.8 mg/mL) at $1.5 \times 10^6$ cells/60-mm dish such that cells were 80% confluent at the time of compound addition. Tritiated compound is incubated at 2 µM in the cell medium for 3 or 23 h. Cells are collected, washed with phosphate-buffered saline, and counted. The cells are then extracted in 70% methanol, 20 mM EDTA, 20 mM EGTA, and centrifuged. The lysate is dried, and radiolabeled nucleotides are analyzed using an ion-pair reverse phase (C-18) HPLC on a Waters Millenium system connected to an in-line β-RAM scintillation detector (IN/US Systems). The HPLC mobile phases consists of (a) 10 mM potassium phosphate with 2 mM tetrabutylammonium hydroxide and (b) 50% methanol containing 10 mM potassium phosphate with 2 mM tetrabutylammonium hydroxide. Peak identification is made by comparison of retention times to standards. Activity is expressed as picomoles of nucleotide detected in $10^6$ HuH-7 or HBI10A cells.

Part Two

The compounds of the present invention were evaluated for their ability to penetrate cells (human hepatoma cell line, hepatocytes) and undergo intracellular conversion to the triphosphate. The method utilized a variety of cell lines and compounds. Following the incubation of compounds with cells, samples are extracted and quantified by HPLC.

Cells are prepared according to the following protocols:
Cells in suspension: for cryopreserved cells the protocol by In Vitro Technologies (Edison, N.J., USA) for cryopreserved cell handling was followed.

For fresh cells preparation the protocol published in Xenobiotica 2005, 35 (1035-54); Giuliano C et al. was followed.

Cells were resuspended to an appropriate cell density (generally 10⁶ cells/mL; single donor or pool of 10 donors) in Hepatocyte Basal medium (Clonetics, CC-3199) and 0.2 mL/well were transferred to sterile 96 well round bottom assay plate (Costar 3788).

Compounds were added in DMSO at 1:1000 dilution, mixed by gentle swirling and incubated at 37° C. under carbogen in a Dubnoff Metabolic Shaking Incubator. Aliquots of the cell suspension were removed at different times, centrifuged at 4° C. for 20 seconds. For adherent cell lines the cells were plated out approximately 1 day in advance in 6-well tissue-culture treated plates in appropriate media and incubated at 37° C./5% $CO_2$. 24 hours after plating, cells were treated with compounds diluted at 1:1000 and incubated for an appropriate period of time at 37° C./5% $CO_2$. In all cases the incubation media was removed by aspiration and then the cells were extracted with cold 70% MeOH, 20 mM EDTA and 20 mM EGTA and centrifuged. The lysate was dried under nitrogen, purified by solid-phase extraction, and stored at −20° C. until analysis.

The dried lysate was analyzed using ZIC-HILIC SeQuant column (100×2.1 mm, 5 μm) on a Agilant 1100 HPLC connected to an API 4000 mass-spectrometer equipped with an electrospray interface (ESI). The mass spectrometer was operated in negative ion electrospray mode. The HPLC mobile phases consisted of: Eluent A: Water with 0.1% formic acid. B: Acetonitrile with 0.1% formic acid. Peak identification was made by comparison of retention times to standards. Activity was expressed as area under the concentration curve (AUC, μMxh).

Representative compounds were incubated with human hepatocytes for 2 hours and shown to form high levels of nucleoside triphosphate (Table 4).

TABLE 4

| Example No. | Human Hepat. AUC (μM × h)[a] |
|---|---|
| 3 | 13/133 |
| 5 | 36/34 |
| 6 | 46/55 |
| 7 | 43/40 |
| 8 | 86[b] |
| 9 | 120/54 |
| 10 | 157/148 |
| 11 | 260/104 |
| 12 | 50/14 |
| 13 | 47/112 |
| 14 | 40/54 |
| 17 | 130/190 |
| 18 | 20/55 |
| 22 | 31/19 |

[a]Values refer to first and second eluting diastereomers, respectively.
[b]Mixture of diastereomers was tested.

The nucleoside aryl phosphoramidates of the present invention are also evaluated for cellular toxicity and anti-viral specificity in the counterscreens described below.

C. Counterscreens:

The ability of the nucleoside aryl phosphoramidates of the present invention to inhibit human DNA polymerases can be measured in the following assays.

a. Inhibition of Human DNA Polymerases Alpha and Beta:
Reaction Conditions:
50 μL reaction volume
Reaction buffer components:
20 mM Tris-HCl, pH 7.5
200 μg/mL bovine serum albumin
100 mM KCl
2 mM β-mercaptoethanol
10 mM $MgCl_2$
1.6 μM dA, dG, dC, dTTP
α-³³P-dATP
Enzyme and Template:
0.05 mg/mL gapped fish sperm DNA template
0.01 U/μL DNA polymerase α or β
Preparation of Gapped Fish Sperm DNA Template:
Add 5 μL 1M $MgCl_2$ to 500 μL activated fish sperm DNA (USB 70076);
Warm to 37° C. and add 30 μL of 65 U/μL of exonuclease III (GibcoBRL 18013-011);
Incubate 5 min at 37° C.;
Terminate reaction by heating to 65° C. for 10 min;
Load 50-100 μL aliquots onto Bio-spin 6 chromatography columns (Bio-Rad 732-6002) equilibrated with 20 mM Tris-HCl, pH 7.5;
Elute by centrifugation at 1,000×g for 4 min;
Pool eluate and measure absorbance at 260 nm to determine concentration.

The DNA template is diluted into an appropriate volume of 20 mM Tris-HCl, pH 7.5 and the enzyme is diluted into an appropriate volume of 20 mM Tris-HCl, containing 2 mM β-mercaptoethanol, and 100 mM KCl. Template and enzyme are pipetted into microcentrifuge tubes or a 96 well plate. Blank reactions excluding enzyme and control reactions excluding test compound are also prepared using enzyme dilution buffer and test compound solvent, respectively. The reaction is initiated with reaction buffer with components as listed above. The reaction is incubated for 1 hour at 37° C. The reaction is quenched by the addition of 20 μL 0.5M EDTA. 50 μL of the quenched reaction is spotted onto Whatman DE81 filter disks and air dried. The filter disks are repeatedly washed with 150 mL 0.3M ammonium formate, pH 8 until 1 mL of wash is <100 cpm. The disks are washed twice with 150 mL absolute ethanol and once with 150 mL anhydrous ether, dried and counted in 5 mL scintillation fluid.

The percentage of inhibition is calculated according to the following equation: % inhibition=[1−(cpm in test reaction−cpm in blank)/(cpm in control reaction−cpm in blank)]×100.

b. Inhibition of Human DNA Polymerase Gamma:

The potential for inhibition of human DNA polymerase gamma can be measured in reactions that include 0.5 ng/μL enzyme; 10 μM dATP, dGTP, dCTP, and TTP; 2 μCi/reaction [α-³³P]-dATP, and 0.4 μg/μL activated fish sperm DNA (purchased from US Biochemical) in a buffer containing 20 mM Tris pH8, 2 mM β-mercaptoethanol, 50 mM KCl, 10 mM $MgCl_2$, and 0.1 μg/μL BSA. Reactions are allowed to proceed for 1 h at 37° C. and are quenched by addition of 0.5 M EDTA to a final concentration of 142 mM. Product formation is quantified by anion exchange filter binding and scintillation counting. Compounds are tested at up to 50 μM.

The percentage of inhibition is calculated according to the following equation: % inhibition=[1−(cpm in test reaction−cpm in blank)/(cpm in control reaction−cpm in blank)]×100.

The ability of the nucleoside aryl phosphoramidates of the present invention to inhibit HIV infectivity and HIV spread is measured in the following assays:

c. HIV Infectivity Assay

Assays can be performed with a variant of HeLa Magi cells expressing both CXCR4 and CCR5 selected for low background β-galactosidase (β-gal) expression. Cells are infected for 48 h, and β-gal production from the integrated HIV-1 LTR promoter is quantified with a chemiluminescent substrate (Galactolight Plus, Tropix, Bedford, Mass.). Inhibitors are titrated (in duplicate) in twofold serial dilutions starting at 100 μM; percent inhibition at each concentration is calculated in relation to the control infection.

d. Inhibition of HIV Spread

The ability of the compounds of the present invention to inhibit the spread of the human immunedeficiency virus (HIV) can be measured by the method described in U.S. Pat. No. 5,413,999 (May 9, 1995), and J. P. Vacca, et al., *Proc. Natl. Acad. Sci.*, 91: 4096-4100 (1994), which are incorporated by reference herein in their entirety.

The nucleoside aryl phosphoramidates of the present invention are also screened for cytotoxicity against cultured hepatoma (HuH-7) cells containing a subgenomic HCV Replicon in an MTS cell-based assay as described in the assay below. The HuH-7 cell line is described in H. Nakabayashi, et al., *Cancer Res.*, 42: 3858 (1982).

e. Cytotoxicity Assay:

Cell cultures can be prepared in appropriate media at concentrations of approximately $1.5 \times 10^5$ cells/mL for suspension cultures in 3 day incubations and $5.0 \times 10^4$ cells/mL for adherent cultures in 3 day incubations. 99 μL of cell culture are transferred to wells of a 96-well tissue culture treated plate, and 1 μL of 100-times final concentration of the test compound in DMSO is added. The plates are incubated at 37° C. and 5% $CO_2$ for a specified period of time. After the incubation period, 20 μL of CellTiter 96 Aqueous One Solution Cell Proliferation Assay reagent (MTS) (Promega) is added to each well and the plates are incubated at 37° C. and 5% $CO_2$ for an additional period of time up to 3 h. The plates are agitated to mix well and absorbance at 490 nm is read using a plate reader. A standard curve of suspension culture cells is prepared with known cell numbers just prior to the addition of MTS reagent. Metabolically active cells reduce MTS to formazan. Formazan absorbs at 490 nm. The absorbance at 490 nm in the presence of compound is compared to absorbance in cells without any compound added.

REFERENCE

Cory, A. H. et al., "Use of an aqueous soluble tetrazolium/formazan assay for cell growth assays in culture," *Cancer Commun.* 3: 207 (1991).

The following assays can be employed to measure the activity of the compounds of the present invention against other RNA-dependent RNA viruses:

a. Determination of In Vitro Antiviral Activity of Compounds Against Rhinovirus (Cytopathic Effect Inhibition Assay):

Assay conditions are described in the article by Sidwell and Huffman, "Use of disposable microtissue culture plates for antiviral and interferon induction studies," *Appl. Microbiol.* 22: 797-801 (1971).

Viruses:

Rhinovirus type 2 (RV-2), strain HGP, is used with KB cells and media (0.1% $NaHCO_3$, no antibiotics) as stated in the Sidwell and Huffman reference. The virus, obtained from the ATCC, is from a throat swab of an adult male with a mild acute febrile upper respiratory illness. Rhinovirus type 9 (RV-9), strain 211, and rhinovirus type 14 (RV-14), strain Tow, are also obtained from the American Type Culture Collection (ATCC) in Rockville, Md. RV-9 is from human throat washings and RV-14 is from a throat swab of a young adult with upper respiratory illness. Both of these viruses are used with HeLa Ohio-1 cells (Dr. Fred Hayden, Univ. of VA) which are human cervical epitheloid carcinoma cells. MEM (Eagle's minimum essential medium) with 5% Fetal Bovine serum (FBS) and 0.1% $NaHCO_3$ is used as the growth medium.

Antiviral test medium for all three virus types was MEM with 5% FBS, 0.1% $NaHCO_3$, 50 μg gentamicin/mL, and 10 mM $MgCl_2$.

2000 μg/mL is the highest concentration used to assay the compounds of the present invention. Virus was added to the assay plate approximately 5 min after the test compound. Proper controls are also run. Assay plates are incubated with humidified air and 5% $CO_2$ at 37° C. Cytotoxicity is monitored in the control cells microscopically for morphologic changes. Regression analysis of the virus CPE data and the toxicity control data gives the ED50 (50% effective dose) and CC50 (50% cytotoxic concentration). The selectivity index (SI) is calculated by the formula: SI=CC50÷ED50.

b. Determination of In Vitro Antiviral Activity of Compounds Against Dengue, Banzi, and Yellow Fever (CPE Inhibition Assay)

Assay details are provided in the Sidwell and Huffman reference above.

Viruses:

Dengue virus type 2, New Guinea strain, is obtained from the Center for Disease Control. Two lines of African green monkey kidney cells are used to culture the virus (Vero) and to perform antiviral testing (MA-104). Both Yellow fever virus, 17D strain, prepared from infected mouse brain, and Banzi virus, H 336 strain, isolated from the serum of a febrile boy in South Africa, are obtained from ATCC. Vero cells are used with both of these viruses and for assay.

Cells and Media:

MA-104 cells (BioWhittaker, Inc., Walkersville, Md.) and Vero cells (ATCC) are used in Medium 199 with 5% FBS and 0.1% $NaHCO_3$ and without antibiotics.

Assay medium for dengue, yellow fever, and Banzi viruses is MEM, 2% FBS, 0.18% $NaHCO_3$ and 50 μg gentamicin/mL. Antiviral testing of the compounds of the present invention is performed according to the Sidwell and Huffman reference and similar to the above rhinovirus antiviral testing. Adequate cytopathic effect (CPE) readings are achieved after 5-6 days for each of these viruses.

c. Determination of In Vitro Antiviral Activity of Compounds Against West Nile Virus (CPE Inhibition Assay)

Assay details are provided in the Sidwell and Huffman reference cited above. West Nile virus, New York isolate derived from crow brain, is obtained from the Center for Disease Control. Vero cells are grown and used as described above. Test medium is MEM, 1% FBS, 0.1% $NaHCO_3$ and 50 μg gentamicin/mL.

Antiviral testing of the compounds of the present invention can be performed following the methods of Sidwell and Huffman which are similar to those used to assay for rhinovirus activity. Adequate cytopathic effect (CPE) readings are achieved after 5-6 days.

d. Determination of In Vitro Antiviral Activity of Compounds Against Rhino, Yellow Fever, Dengue, Banzi, and West Nile Viruses (Neutral Red Uptake Assay)

After performing the CPE inhibition assays above, an additional cytopathic detection method can be used which is described in "Microtiter Assay for Interferon: Microspectrophotometric Quantitation of Cytopathic Effect," *Appl. Environ. Microbiol.* 31: 35-38 (1976). A Model EL309 microplate reader (Bio-Tek Instruments Inc.) is used to read the assay plate. $ED_{50}$'s and $CD_{50}$'s are calculated as above.

Example of a Pharmaceutical Formulation

As a specific embodiment of an oral composition of a compound of the present invention, 50 mg of the compound of Example 1 or Example 2 can be formulated with sufficient finely divided lactose to provide a total amount of 580 to 590 mg to fill a size 0 hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for severity of the HCV infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of the structural formula I:

[Structural formula I]

or a pharmaceutically acceptable salt thereof; wherein

B is

[Structural formulas for B]

wherein the asterisk (*) denotes the point of attachment to the rest of the compound;

n is 0, 1, or 2,

X is a bond or O;

Ar is phenyl, naphthyl, pyridinyl, pyrimidinyl, pyrazinyl, pyridazinyl, indolyl, quinolinyl, or isoquinolinyl, wherein Ar is optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^1$ is hydrogen, methyl, or, fluoromethyl;

$R^2$ is fluoro or $OR^{10}$;

$R^3$ is selected from the group consisting or hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

[Structural formula]

$R^{10}$ is selected from the group consisting of hydrogen, methyl, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

[Structural formula]

or $R^3$ and $R^{10}$ together with the oxygen atoms to which they are attached form a five-membered cyclic carbonate or an acetonide;

$R^4$ is hydrogen, $C_{1-6}$ alkyl, phenyl, or benzyl;
  wherein alkyl is optionally substituted with one substituent selected from the group consisting of fluorine, hydroxy, methoxy, amino, carboxy, carbamoyl, guanidino, mercapto, methylthio, 1H-imidazolyl, and 1H-indol-3-yl; and wherein phenyl and benzyl are optionally substituted with one to two substituents independently selected from the group consisting of halogen, hydroxy, and methoxy;

$R^5$ is hydrogen or $C_{1-3}$ alkyl;

or $R^4$ and $R^5$ together with the carbon atom which they are attached form a 3- to 6-membered aliphatic spirocyclic ring system;

$R^6$ is $C_{1-16}$ alkyl, $C_{2-20}$ alkenyl, $(CH_2)_n C_{3-6}$ cycloalkyl, phenyl, benzyl, or adamantyl; wherein alkyl, alkenyl, cycloalkyl, and adamantyl are optionally substituted with one to three substituents independently selected from amino $C_{1-4}$ alkylamino, di-($C_{1-4}$ alkyl)amino, halogen, hydroxy, carboxy, and $C_{1-4}$ alkoxy, and wherein phenyl and benzyl are optionally substituted with one to three substituents independently selected from halogen, hydroxy, cyano, $C_{1-4}$ alkoxy, trifluoromethyl; and trifluoromethoxy;

$R^7$ is hydrogen, $C_{1-5}$ alkyl, or phenyl $C_{0-2}$ alkyl;

$R^8$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl;

$R^9$ is hydrogen, alkylcarbonyl, or $C_{1-8}$ alkyloxycarbonyl;

$R^{11}$ is hydrogen $C_{1-3}$ alkyl;

or $R^{11}$ together with $R^{13}$ form a ring of formula:

[Structural formula]

$R^{12}$ is hydrogen or $C_{1-3}$ alkyl;

$R^{13}$ is hydrogen or $C_{1-3}$ alkyl; and $R^{14}$ is hydrogen or $C_{1-3}$ alkyl, or $C_{1-8}$ alkylcarbonyl.

2. The compound of claim 1, or a pharmaceutically acceptable salt thereof, wherein the compound is a compound of Formula I-A:

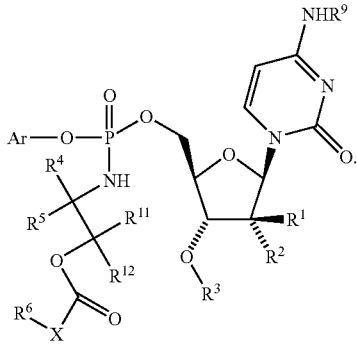

(I-A)

3. The compound of claim 1, or a pharmaceutically acceptable salt thereof, wherein the compound is a compound of Formula I-B1:

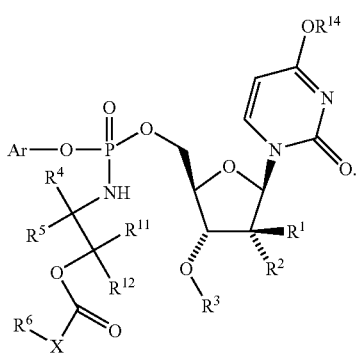

(I-B1)

4. The compound of claim 2, or a pharmaceutically acceptable salt thereof, wherein $R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, and an amino acyl residue of structural formula:

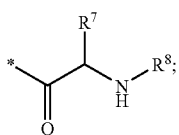

R is selected from the group consisting of hydrogen, methyl, $C_{1-16}$ alkylcarbonyl, $C_{2-18}$ alkenylcarbonyl, $C_{1-10}$ alkyloxycarbonyl; $C_{3-6}$ cycloalkylcarbonyl, $C_{3-6}$ Cycloalkyloxycarbonyl, and an amino acyl residue of structural formula:

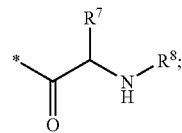

or $R^3$ and $R^{10}$ together with the oxygen atoms to which they are attached forma a five-membered cyclic carbonate; and $R^{11}$ is hydrogen or $C_{1-3}$ alkyl.

5. The compound of claim 1, or a pharmaceutically acceptable salt thereof, wherein $R^1$ is methyl or fluoromethyl, $R^2$ is hydroxy, and $R^3$ is hydrogen.

6. The compound of claim 5, or a pharmaceutically acceptable salt thereof, wherein $R^1$ is methyl.

7. The compound of claim 1, or a pharmaceutically acceptable salt thereof, wherein $R^1$ is methyl or fluoromethyl, $R^2$ is fluoro, and $R^3$ is hydrogen.

8. The compound of claim 7, or a pharmaceutically acceptable salt thereof, wherein $R^1$ is methyl.

9. The compound of claim 1, or a pharmaceutically acceptable salt thereof, wherein X is a bond.

10. The compound of claim 1, or a pharmaceutically acceptable salt thereof, wherein Ar is a phenyl optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl) amino, $C_{1-4}$ alkylcarbonyl, $C_{1-4}$ alkylcarbonyloxy, and $C_{1-4}$ alkyloxycarbonyl.

11. The compound of claim 10, or a pharmaceutically acceptable salt thereof, wherein Ar is unsubstituted phenyl.

12. The Compound of claim 1, or a pharmaceutically acceptable salt thereof, wherein Ar is indolyl.

13. The compound of claim 12, or a pharmaceutically acceptable salt thereof, wherein Ar is 1H-indol-5-yl.

14. The compound of claim 1, or a pharmaceutically acceptable salt thereof, wherein $R^5$, $R^{11}$, and $R^{12}$ are each hydrogen, and $R^4$ is selected from the group consisting of hydrogen, methyl, ethyl, n-propyl, isopropyl, isobutyl, n-butyl, 2-methyl-1-propyl, hydroxymethyl, fluoromethyl, mercaptomethyl, carboxymethyl, carbamoylmethyl, 1-hydroxyethyl, 2-carboxyethyl, 2-carbamoylethyl, 2-methylthioethyl, 4-amino-1-butyl, 3-amino-1-propyl, 3-guanidino-1-propyl, 1H-imidazol-4-ylmethyl, phenyl, benzyl, 4-hydroxybenzyl, and 1H-indol-3-ylmethyl.

15. The compound of claim 14, or a pharmaceutically acceptable salt thereof, wherein $R^4$ is methyl or benzyl.

16. The compound of claim 1, or a pharmaceutically acceptable salt thereof, wherein X is a bond, and $R^6$ is $C_{1-8}$ alkyl, cyclohexyl, or cyclopentyl.

17. The compound of claim 16, or a pharmaceutically acceptable salt thereof, wherein $R^6$ is $C_{1-4}$ alkyl.

18. The compound of claim 1, or a pharmaceutically acceptable salt thereof, wherein X a bond, Ar is phenyl, $R^4$ is methyl or benzyl, $R^6$ is $C_{1-4}$ alkyl, and $R^5$, $R^{11}$, and $R^{12}$ are each hydrogen.

19. The compound of claim 18, or a pharmaceutically acceptable salt thereof, wherein $R^1$ is methyl, $R^2$ is hydroxy, and $R^3$ is hydrogen.

20. The compound of claim 3, or a pharmaceutically acceptable salt thereof, wherein the compound is a compound of Formula II-A:

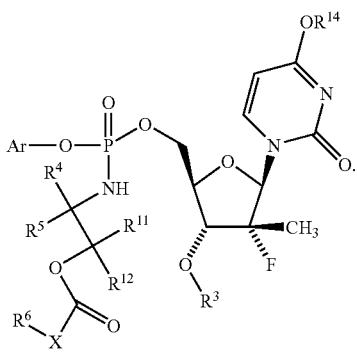

(II-A)

21. The compound of claim 20, or a pharmaceutically acceptable salt thereof, wherein the compound is a compound of Formula II-B:

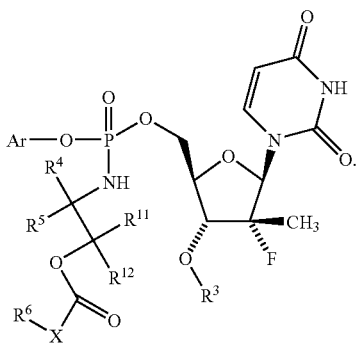

(II-B)

22. The compound of claim 1, or a pharmaceutically acceptable salt thereof, wherein the compound is a compound of Formula III:

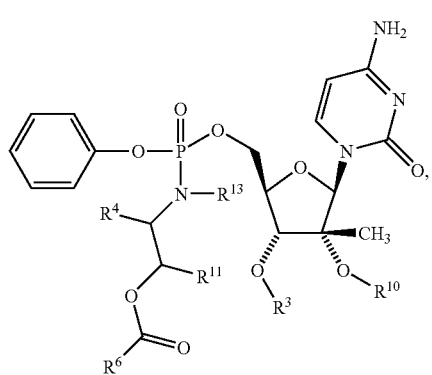

(III)

wherein:
$R^3$ is H;
$R^{10}$ is H;
or $R^3$ and $R^{10}$ together with the oxygen atoms to which they are attached form acetonide;
$R^4$ is methyl, ethyl, n-propyl, isopropyl, n-butyl, isobutyl, t-butyl, $CH(CH_3)CH_2CH_3$, or benzyl;
$R^6$ is methyl, ethyl, n-propyl, isopropyl, n-butyl, isobutyl, t-butyl, $CH(CH_2CH_2CH_3)_2$, 3-pentyl, cyclopentyl, cycloheptyl, or phenyl;

$R^{11}$ is H or $CH_3$;
$R^{13}$ is hydrogen or $CH_3$;
or alternatively when $R^4$ is H, $R^{11}$ together with $R^{13}$ form a ring of formula:

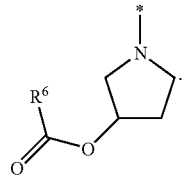

23. A compound of claim 1 which is selected from the group consisting of:
- 5'-O-[{(1S)-2-[(2,2-Dimethylpropanoyl)-oxy]-1-methylethyl}-amino)-(phenoxy)-phosphoryl]-2'-C-methylcytidine;
- 5'-O-[{[(1S)-2-(Butyryloxy)-1-methylethyl]-amino}-(phenoxy)-phosphoryl]-2'-C-methylcytidine;
- 5'-O-[[[2-(2,2-Dimethyl-1-oxopropoxy)-ethyl]-amino]-(phenoxy)-phosphinyl]-2'-C-methylcytidine;
- 5'-O-[[[2-(2,2-Methyl-1-oxopropoxy)-ethyl]-amino]-(phenoxy)-phosphinyl]-2'-C-methylcytidine;
- 5'-O-[{[(1S)-1-Methyl-2-(2-methyl-1-oxopropoxy)ethyl]-amino}-(phenoxy)-phosphinyl]-2'-C-methylcytidine;
- 5'-O-[{[(1S,2S)-1-[(2,2-Dimethyl-1-oxopropoxy)methyl]-2-methylbutyl]amino}-(phenoxy)-phosphoryl]-2'-C-methylcytidine;
- 5'-O-[[[(1S)-1-[(2,2-dimethyl-1-oxopropoxy)methyl]pentyl]amino]-(phenoxy)-phosphinyl]-2'-C-methylcytidine;
- 5'-O-[[[(1S)-2-[(2,2-dimethyl-1-oxopropoxy)-1-(phenylmethyl)]-ethyl]amino]-(phenoxy)-phosphinyl]-2'-C-methylcytidine;
- 5'-O-[[[2-[(1-oxo-2-propylpentyl)oxy]ethyl]amino]phenoxyphosphinyl]-2'-C-methylcytidine;
- 5'-O-[[[(1S)-2-(1H-indol-3-yl)-1-(2-methyl-1-oxopropoxy)methyl]ethyl]amino]phenoxyphosphinyl]-2'-C-methylcytidine;
- 5'-O-[[[(1S)-2-(2-methyl-1-oxopropoxy)-1-(phenylmethyl)]ethyl]amino]phenoxyphosphinyl]-2'-C-methylcytidine;
- 5'-O-[[[(2S)-2-(2-methyl-1-oxopropoxy)propyl]amino]phenoxyphosphinyl]-2'-C-methylcytidine;
- 5'-O-[[[(2R)-2-(2-methyl-1-oxopropoxy)propyl]amino]phenoxyphosphinyl]-2'-C-methylcytidine;
- 5'-O-[[[(1S)-2-(2,2-dimethyl-1-oxopropoxy)-1-(phenylmethyl)ethyl]amino]henoxyphosphinyl]-2'-C-methyl-2',3'-O-(1-methylethylidene)-cytidine;
- 5'-O-[[[(1S)-1-[(2,2-dimethyl-1-oxopropoxy)methyl]pentyl]amino]phenoxyphosphinyl]-2'-C-methyl-2',3'-O-(1-methylethylidene)-cytidine;
- 5'-O-[[[2-(benzoyloxy)ethyl]amino]phenoxyphosphinyl]-2'-C-methyl-cytidine;
- 5'-O—[({(1S)-1-benzyl-2-[(2,2-dimethylpropanoyl)oxy]ethyl}amino) (phenoxy)phosphoryl]-2'-C-methylcytidine;
- 5'-O-[{[2-(acetyloxy)ethyl]amino}(phenoxy)phosphoryl]-2'-C-methylcytidine;
- 2'-C-methyl-5'-O-[[methyl[2-(2-methyl-1-oxopropoxy)ethyl]amino]phenoxyphosphinyl]-cytidine;
- 5'-O—[({2-[(2-ethylbutanoyl)oxy]ethyl}amino)(phenoxy)phosphoryl]-2'-C-methylcytidine;

5'-O—[({2-[(cyclohepytlcarbonyl)oxy]ethyl}amino)(phenoxy)phosphoryl]-2'-C-methylcytidine; and 2'-C-methyl-5'-O-[[(3R)-3-(2-methyl-1-oxopropoxy)-1-pyrrolidinyl]phenoxyphosphinyl]-cytidine, and pharmaceutically acceptable, salts thereof.

24. A pharmaceutical composition comprising a compound of claim 1, or a pharmaceutically acceptable salt thereof, and a pharmaceutically acceptable carrier.

25. A method for the treatment of hepatitis C virus infection in a mammal in need thereof, which comprises administering a compound of claim 1, or a pharmaceutically acceptable salt thereof, to the mammal.

* * * * *